(12) United States Patent
Baumgartner

(10) Patent No.: US 7,597,032 B2
(45) Date of Patent: Oct. 6, 2009

(54) TORQUE WRENCH AS A RATCHET INSTRUMENT FOR THE MEDICAL FIELD

(75) Inventor: Reto Baumgartner, Nuglar (CH)

(73) Assignee: Thommen Medical AG, Waldenburg (CH)

( * ) Notice: Subject to any disclaimer, the term of this patent is extended or adjusted under 35 U.S.C. 154(b) by 188 days.

(21) Appl. No.: 11/662,390

(22) PCT Filed: Mar. 26, 2005

(86) PCT No.: PCT/CH2005/000177

§ 371 (c)(1),
(2), (4) Date: Mar. 9, 2007

(87) PCT Pub. No.: WO2006/029542

PCT Pub. Date: Mar. 23, 2006

(65) Prior Publication Data

US 2008/0070190 A1    Mar. 20, 2008

(30) Foreign Application Priority Data

Sep. 13, 2004  (DE) .................. 20 2004 014 195 U

(51) Int. Cl.
*B25B 23/14* (2006.01)
*B25B 13/46* (2006.01)
(52) U.S. Cl. ............................ 81/467; 81/60
(58) Field of Classification Search .................. 81/467, 81/477, 60–63.2
See application file for complete search history.

(56) References Cited

U.S. PATENT DOCUMENTS

| 2,447,109 | A |   | 8/1948 | Billeter |        |
|-----------|---|---|--------|----------|--------|
| 2,936,661 | A | * | 5/1960 | Hostetter | 81/477 |
| 3,587,307 | A |   | 6/1971 | Newberg  |        |
| 5,597,305 | A |   | 1/1997 | Ray, Sr. |        |
| 5,653,151 | A | * | 8/1997 | Blacklock | 81/60  |

(Continued)

FOREIGN PATENT DOCUMENTS

CH          91 638         11/1921

(Continued)

OTHER PUBLICATIONS

Written Opinion issued by the ISA in connection with International Patent Appln. No. PCT/CH2005/000177.

(Continued)

*Primary Examiner*—Hadi Shakeri
(74) *Attorney, Agent, or Firm*—McCarter & English, LLP

(57) ABSTRACT

A torque wrench (1) is embodied as a ratchet instrument in the medical field. A catch segment (40) which can be displaced in a defined manner is arranged on the periphery of the receiving opening, and the front part thereof is oriented towards the receiving opening. When the torque wrench (1) is actuated in a forward direction, the torque which is to be generated is applied by a forward force (F) exerted by an user, by a deflectable, preferably linear-elastic flexible arm (7). A catch spring extends from the catch segment into the neck area. The catch segment and the catch spring form a single-pieced or several part catch (4). The catch segment and the catch spring are arranged in a channel-shaped space (5). The catch (4) is a single-piece with the neck part or is fixed thereto as a separate component.

10 Claims, 16 Drawing Sheets

U.S. PATENT DOCUMENTS

| | | | | |
|---|---|---|---|---|
| 5,709,137 | A * | 1/1998 | Blacklock | 81/467 |
| 5,734,113 | A | 3/1998 | Vogt et al. | |
| 5,996,453 | A * | 12/1999 | Blacklock | 81/467 |
| 6,109,150 | A | 8/2000 | Saccomanno, III | |
| 6,382,051 | B1 | 5/2002 | Chang | |
| 6,862,955 | B1 * | 3/2005 | Shu-Sui et al. | 81/60 |
| 6,988,430 | B1 * | 1/2006 | Putney et al. | 81/60 |
| 2006/0027049 | A1 * | 2/2006 | Arnold | 81/60 |

FOREIGN PATENT DOCUMENTS

| | | |
|---|---|---|
| DE | 94 02 607 U1 | 4/1994 |
| EP | 0 704 281 A1 | 4/1996 |
| FR | 1 498 385 | 10/1967 |
| GB | 1 104 501 A | 2/1968 |

OTHER PUBLICATIONS

International Search Report issued by the ISA in connection with International Patent Appln. No. PCT/CH2005/000177.

Spiekermann, H, Farbatlanten der Zahnmedizin, vol. 10 Implantologie, Georg Theime Verlag, Stuttgart, 1994, pp. 33, 54 and 55.

* cited by examiner

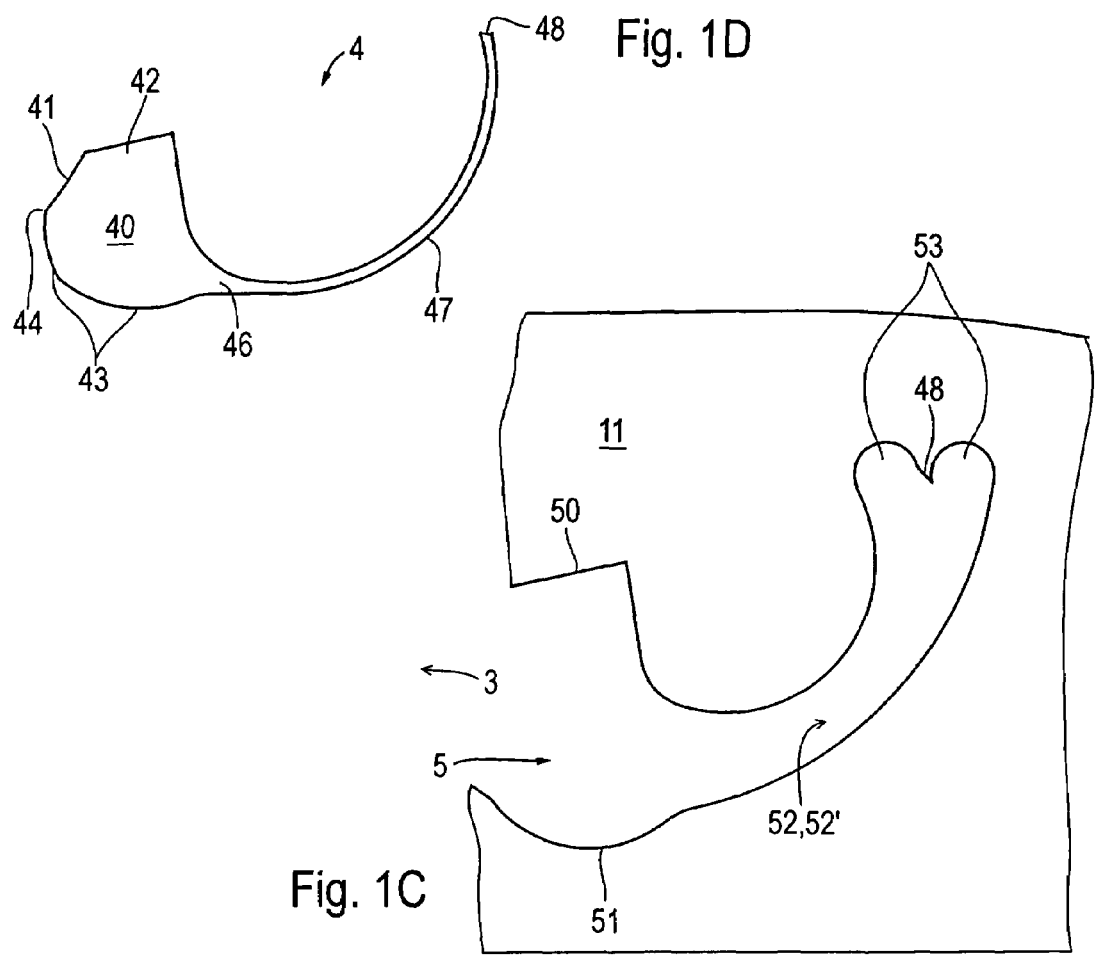
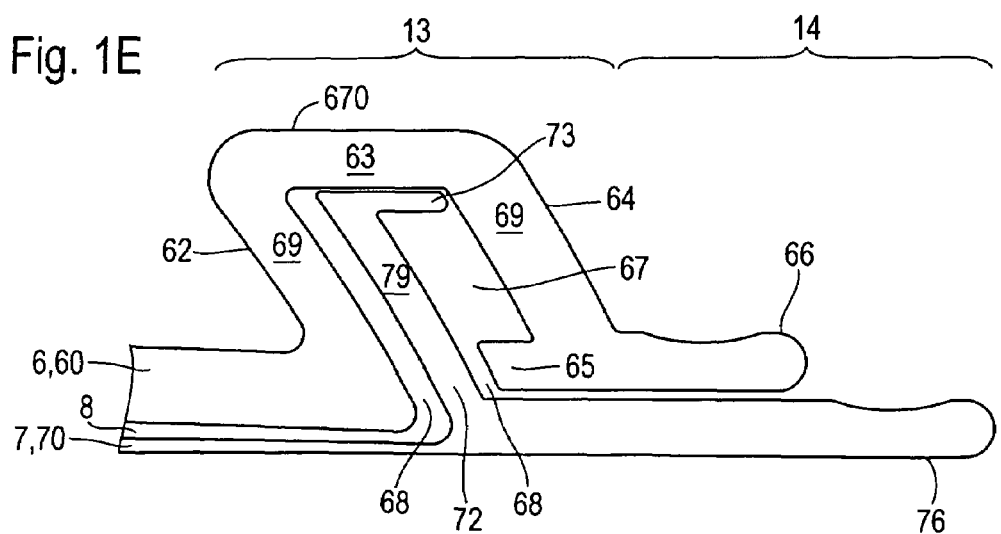

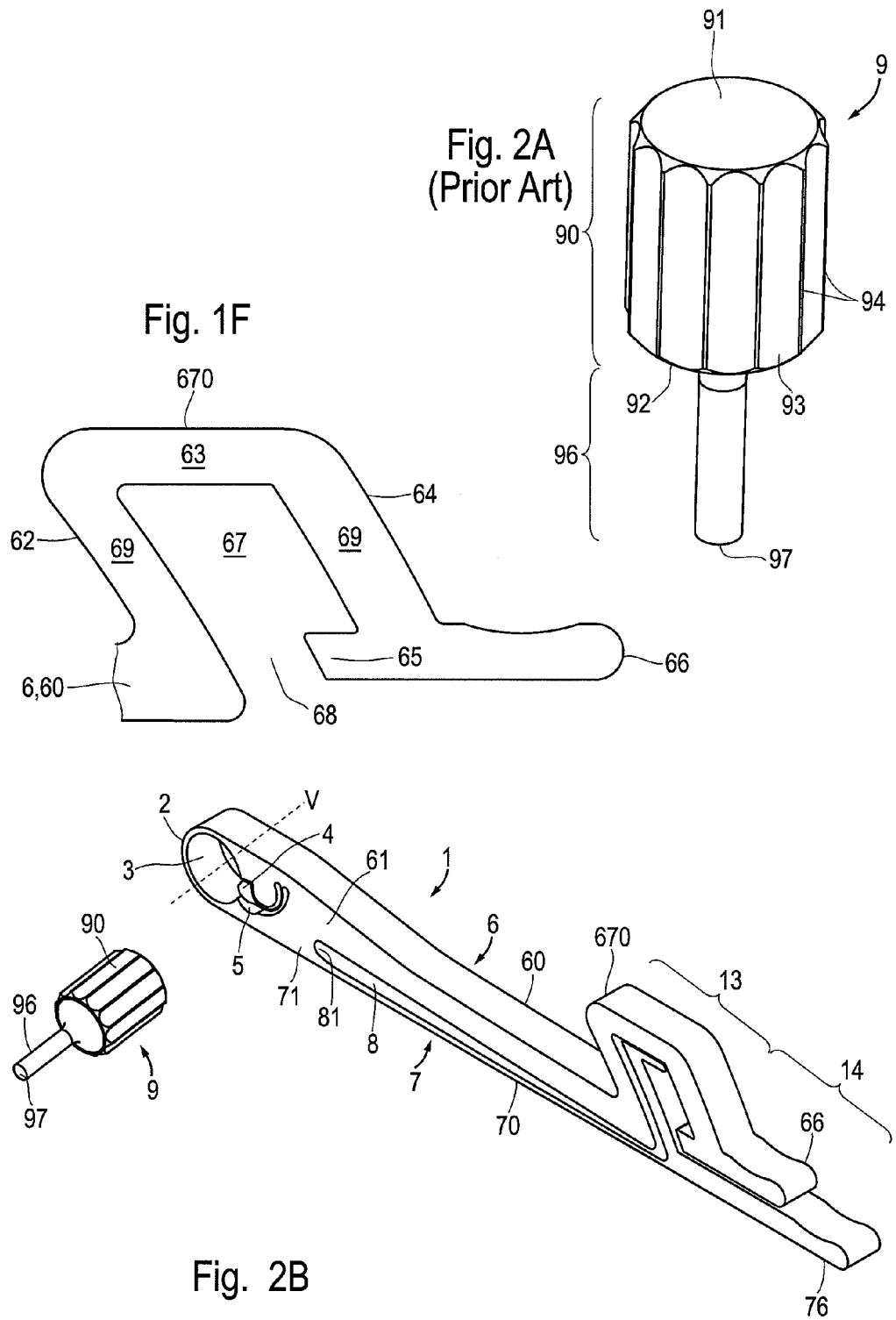

Fig. 5B
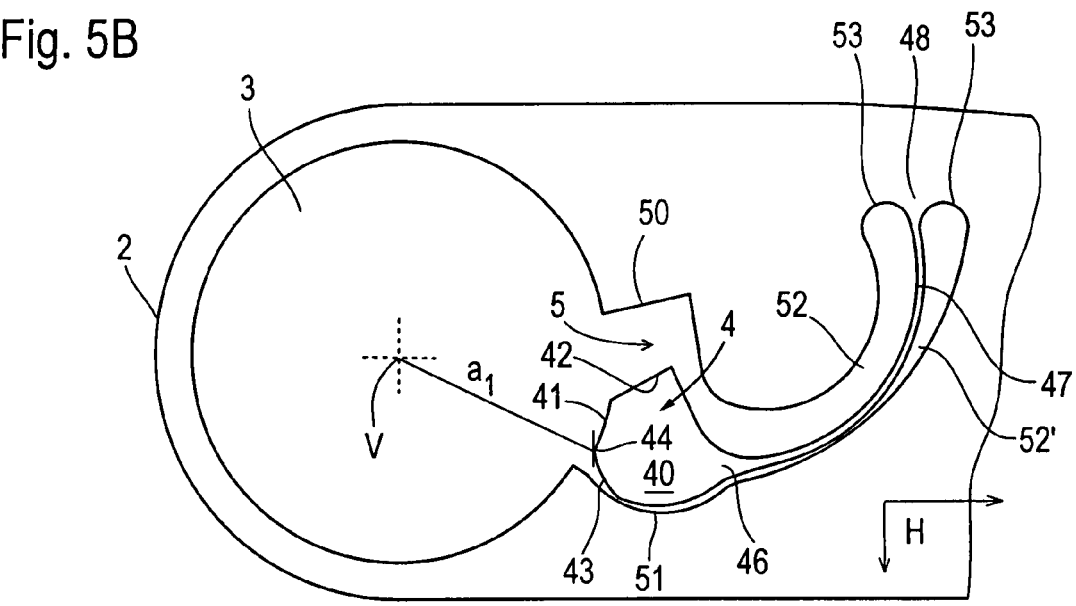
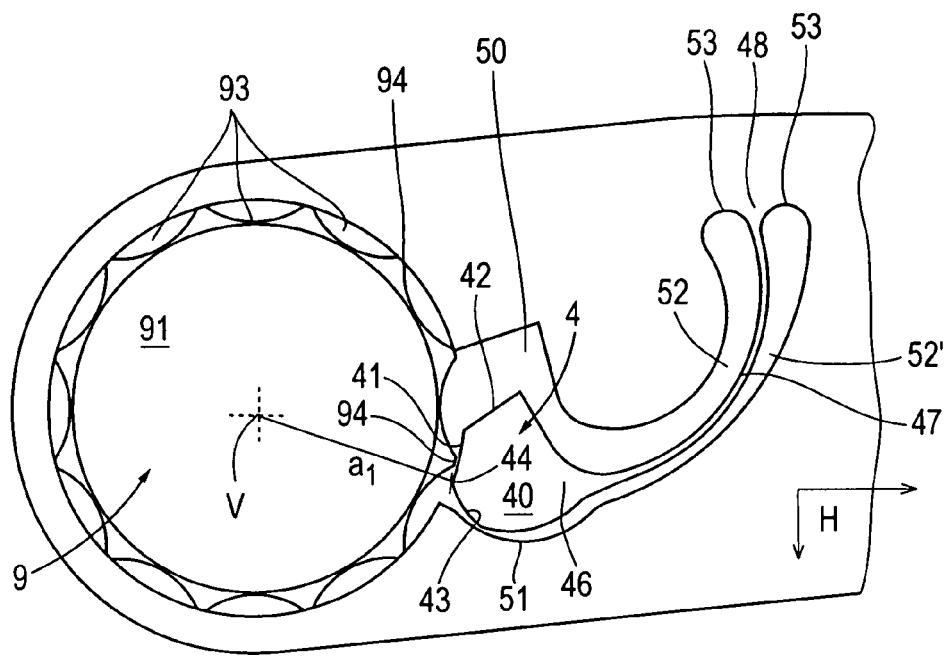
Fig. 5C

Fig. 9A
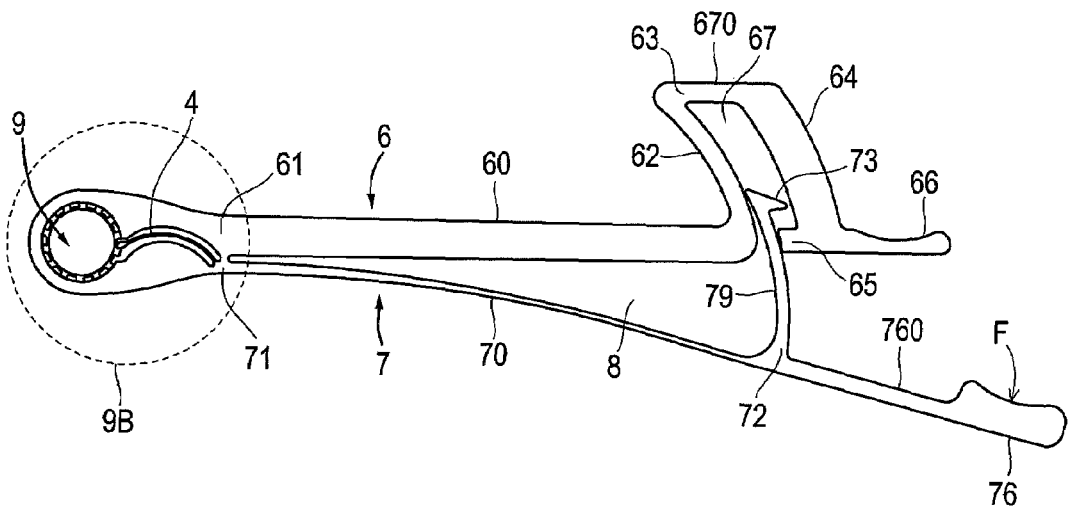
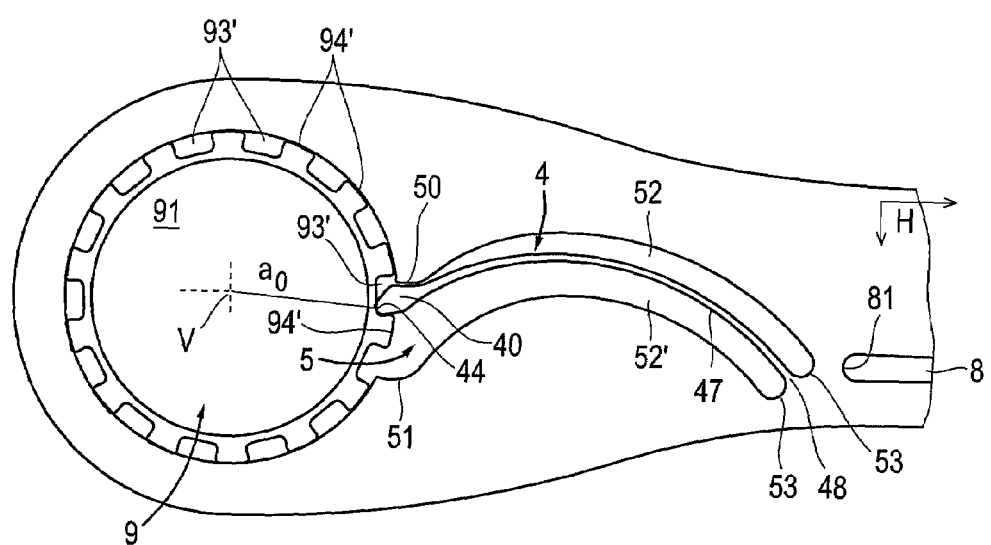
Fig. 9B

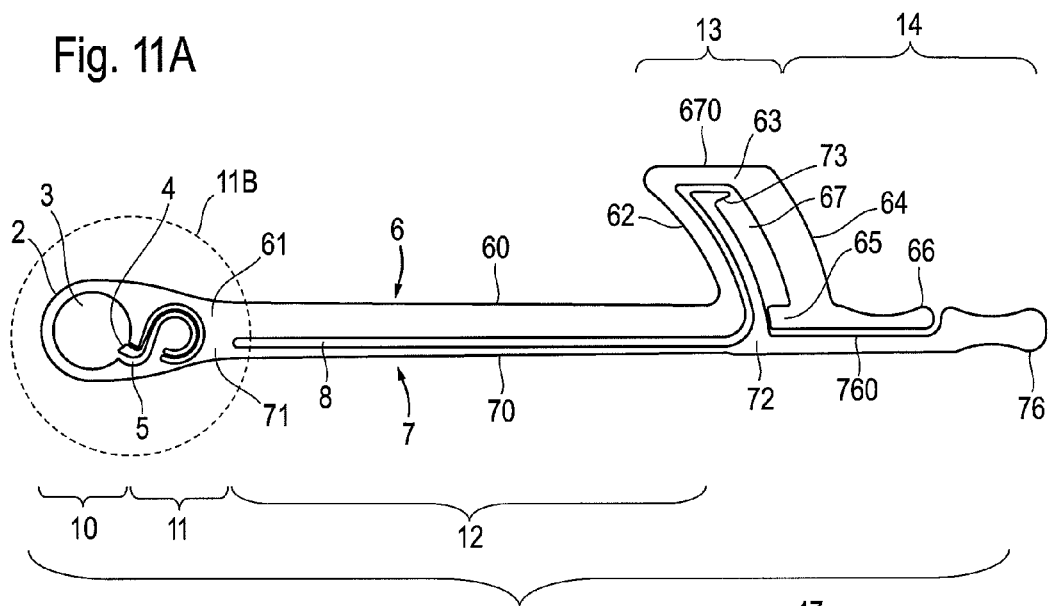
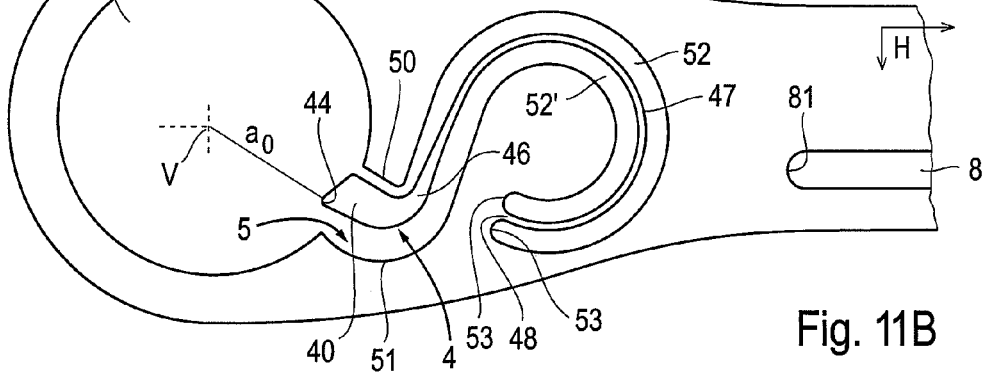

Fig. 12A
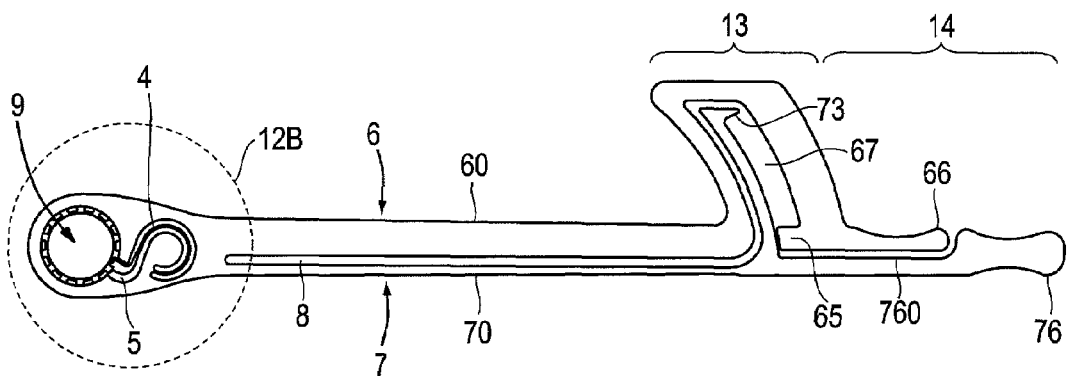
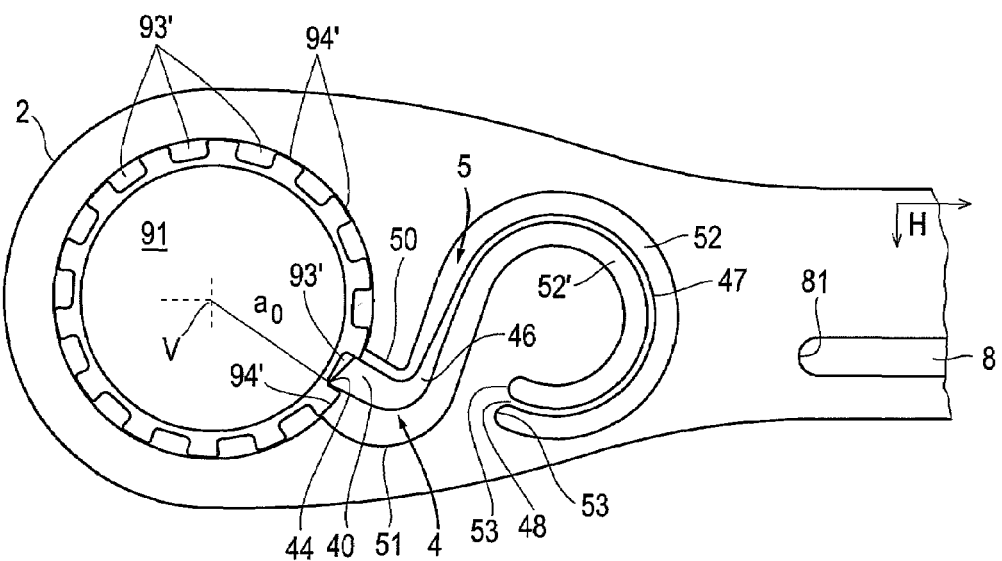
Fig. 12B

Fig. 13A
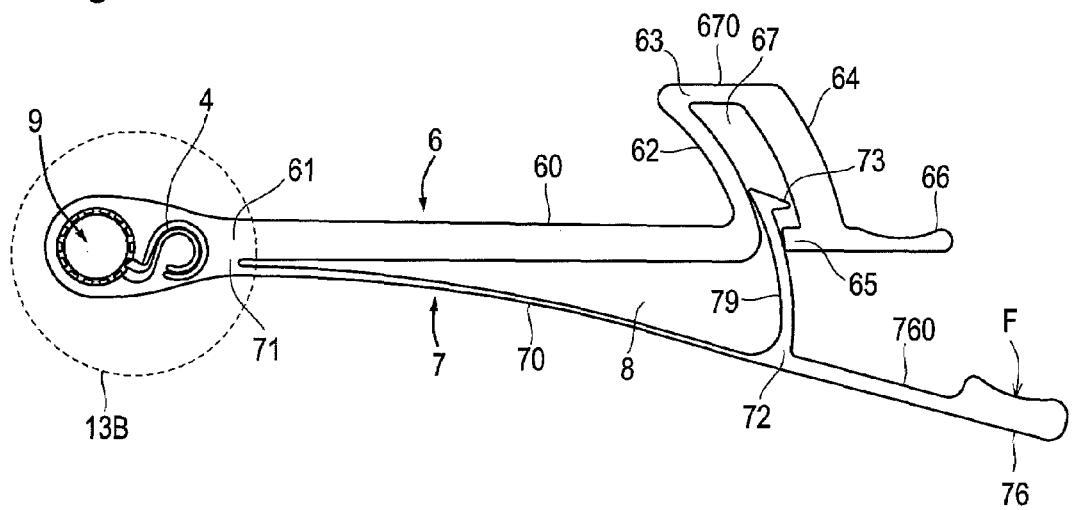
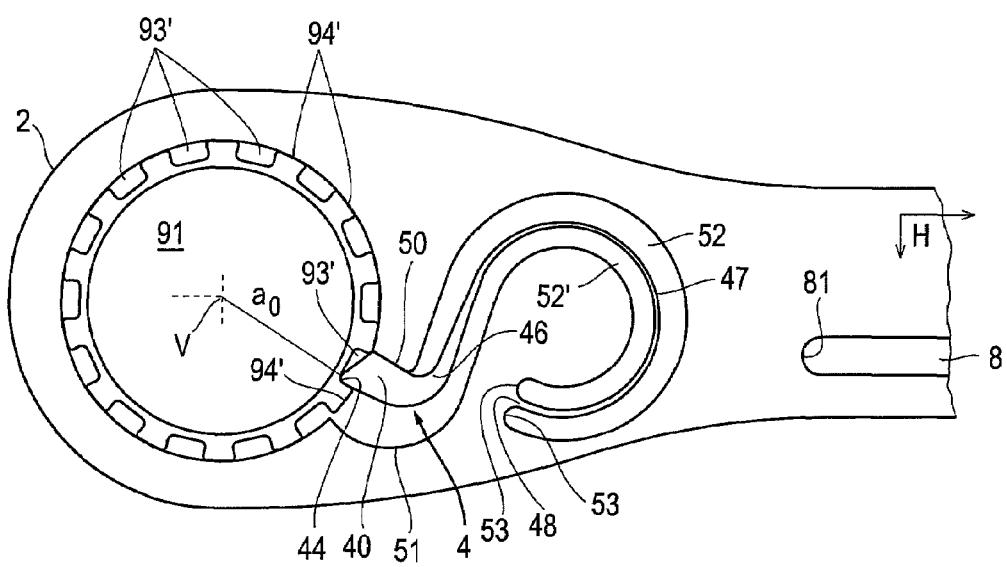
Fig. 13B

TORQUE WRENCH AS A RATCHET INSTRUMENT FOR THE MEDICAL FIELD

FIELD OF APPLICATION OF THE INVENTION

The invention relates to a torque wrench which is designed as a ratchet instrument for use in the medical field, in particular in dental prosthetics. In the case of implants inserted into the jawbone, superstructures are fastened thereon by means of special screws. The reliability of the screw connections requires the latter to be carried out with the torque envisaged in each case. Not enough tightening by way of an excessively low torque may result in the screw connection loosening. Exceeding the optimum torque, i.e. over-tightening, overloads the connecting elements used and increases the risk of the latter rupturing.

PRIOR ART

Torque wrenches having a bending rod and a numerical or at least magnitude-specific display for the tightening torque applied are known in mechanical engineering, e.g. in accordance with FR 1 498 385; U.S. Pat. No. 2,447,109; U.S. Pat. No. 2,936,661 and U.S. Pat. No. 3,587,307. These tools, however, cannot be used as instruments in the medical field just by being miniaturized. U.S. Pat. No. 5,597,305 describes a torque wrench which is suitable specifically for dental prosthetics, but cannot be operated in a reversible ratchet mode. Spiekermann, H.: Farbatlanten der Zahnmedizin, Vol. 10 Implantologie, Georg Thieme Verlag, Stuttgart, 1994, pages 33 and 53, discloses torque wrenches with a ratchet function, although these do not have any display or torque-limiting means, or the tightening torque is limited by means of a relatively complicated slip clutch. In the case of these instruments, the frictional conditions change quickly in an indeterminate manner on account of roughened surfaces. These instruments are therefore very sensitive and have components which require an excessive amount of effort in order to be cleaned.

EP 0 704 281 B1 proposes a torque wrench which has a bending rod and a numerical display for the tightening torque applied and can also be used in the ratchet mode. It is also the case that this instrument comprises a plurality of individual parts, which require dismantling prior to cleaning. U.S. Pat. No. 5,653,151; U.S. Pat. No. 5,709,137 and U.S. Pat. No. 5,996,453 disclose further torque wrenches which also allow the ratchet mode. The ratchet head contains an approximately oval mount in which is located a relatively small star wheel with a central polygon structure for tool insertion. A spring element which pushes against the star wheel is located on the periphery of the mount. Opposite the spring element, the mount has, in some regions along its edge, a toothing formation, which complements the toothing formation of the star wheel. The toothing formation of the star wheel engages in the toothing formation of the mount in the screwing-in direction, so that a tool which has been plugged in rotates along therewith. During the return ratchet movement, the star wheel disengages from the toothing formation along the edge and is pushed against the spring element. U.S. Pat. No. 6,382,051 uses an externally toothed ratchet head in the circular mount of the instrument head. A cavity is provided in the peripheral region of the mount and has a blind hole extending from it into the ratchet head. The blind hole contains the first end of a helical spring, of which the relatively thick central part is located in front of the blind-hole mouth and the thinner second end bears a blocking element which can be moved counter to the spring. The blocking element is located in the cavity, but has its outer toothing formation engaging in the toothing formation of the ratchet head. During the screwing-in movement, the blocking element arrests the ratchet head, whereas, during the return ratchet movement, the blocking element disengages. These instruments require an externally toothed ratchet head which can be displaced in an oval opening or is blocked by a spring-mounted wedge and/or released in the ratchet mode.

OBJECT OF THE INVENTION

In view of the currently available torque wrenches for the medical field having functional and design features which may be considered to be incomplete, it is an object of the invention to provide an instrument which, while being easier to dismantle, is straightforward to clean. At the same time, the intention is for the subsequent effort required for reassembly to be reduced. The geometrical dimensions and the shape of the instrument have to allow straightforward handling in the different positions in a constricted amount of space, e.g. in a patient's mouth, which requires reversible actuation in ratchet mode. The torque wrench has to be designed for use with conventional screwing-in tools. Individual handling and progressive surface roughness must not have any adverse effect. A further object is for it to be possible to monitor and reproduce the torques generated, so that it has to be possible to read the value of each tightening torque applied at any point in time. Finally, it should be possible to mass-produce the torque wrench at efficient production costs.

OVERVIEW OF THE INVENTION

The torque wrench is designed as a ratchet instrument for the medical field and has a head region located at the front, an adjoining neck region, which is followed by a shank region, and a handle region arranged at the rear. These regions extend, in principle, in a common plane. The head region contains an accommodating opening which is enclosed by a surround, which has a center point through which an axis extends. The accommodating opening serves for the insertion of a conventional screwing-in instrument along the extent of the axis, which is perpendicular, at least in principle, to the plane. Arranged on the periphery of the accommodating opening is a catch segment which can be moved to a limited extent and the front portion of which is oriented toward the accommodating opening. The front portion is intended, upon actuation of the torque wrench in the forward direction—that is to say in the screwing-in mode—for coming into carry-along engagement with an outer contour provided on the head of the screwing-in instrument. Upon actuation of the torque wrench in the return direction—that is to say in the ratchet mode—the carry-along engagement between the front portion of the catch segment and the outer contour provided on the head of the screwing-in instrument is released. A flexurally rigid basic branch runs along the torque wrench from the neck region thereof. The characterizing part of the invention comprises the following features:

there is a provided a deflectable, preferably linearly elastic flexible branch via which, upon actuation of the torque wrench in the forward direction, the torque which is to be generated is introduced by means of a forward force exerted by the user;

a catch spring extends into the neck region from the catch segment, and the catch segment and catch spring form a single-piece catch or one which is made up of a number of parts;

the catch segment and the catch spring are arranged in a channel-like free space, which allows both to be deflected in the plane counter to the force of the catch spring; and the catch is formed integrally from the neck region or is fastened thereon as a separate component.

The following features constitute advantageous embodiments of the invention: on its front portion, the catch segment has a front nose, to one side of which is located a second flank and to the other side of which is located a third flank. The free space has a first and a second stop in the region of the mouth opening. The first stop is arranged opposite the second flank. Upon actuation of the torque wrench in the forward direction, the second flank of the at least basically non-deflected catch butts against the first stop. The front nose here is spaced apart at least in principle by the minimum distance from the axis. The second stop, at least in part, is arranged opposite the third flank. Upon actuation of the torque wrench in the return direction, the third flank of the deflected catch has moved toward the second stop or butts against the same. The front nose is then spaced apart by the maximum distance from the axis, the second flank is remote from the first stop and the catch spring has been elastically deformed counter to its restoring force.

The catch spring is in the form of a rectilinear or at least partially curved leaf spring and, on the one hand, merges into the catch segment at a spring outlet and, on the other hand, merges into the neck region at a spring mouth. The front nose of the catch segment is followed, in one direction, by a first flank, this being adjoined by the second flank. The front nose is followed, in the other direction, by the third flank, which extends in a rounded manner in the direction of the spring outlet. The front nose is designed as a point or convexity which is raised in the direction of the accommodating opening. The first stop is formed, at least in principle, as a straight edge and the second stop is of trough-like form. The catch spring, which projects through the free space, divides off a first and a second spring clearance, the proportions of which change as the catch spring moves, and which terminate in a base which is followed by the spring mouth.

The basic branch extends as a longitudinal leg, in the first instance from a transition located in the neck region, via the shank region, into an indicator region and terminates freely in the handle region by way of a basic handle. The flexible branch runs, in the first instance likewise as an elongate longitudinal leg and in principle parallel to the longitudinal leg of the basic branch, into the indicator region from a transition located in the neck region, and terminates freely in the handle region by way of a handle part, which projects beyond the basic handle. The flexible branch may have on its top side, directed toward the basic branch, a depression, in which the stop leg and the basic handle are partially embedded. A cutout is located between the longitudinal leg of the basic branch and the longitudinal leg of the flexible branch and extends into the indicator region from a groove base adjacent to the two transitions.

The indicator region is formed by at least one branching portion of the basic branch, the portion being located between the longitudinal leg and the basic handle, and by at least one branching portion of the flexible branch, this branching portion being located between the longitudinal leg of the flexible branch and the handle part. As the torque wrench is actuated in the forward direction and the flexible branch is deflected, the relative positioning between the at least one branching portion of the basic branch and the at least one branching portion of the flexible branch—starting from the rest position or zero position—undergoes an incremental change which is a measure of the torque generated. A first and a second measuring marking are respectively provided on the at least one branching portion of the basic branch and the at least one branching portion of the flexible branch, it being possible to read from these measuring markings the deflection of the flexible branch, due to the forward force acting thereon, as the torque generated.

As an alternative, the indicator region comprises, in the first instance, a bracket which extends from the longitudinal leg to the basic handle, is formed by the at least one branching portion and encloses a clearance for which a through-passage is provided. In the case of this embodiment, the indicator region also comprises the at least one branching portion of the flexible branch, this branching portion projecting through the through-passage into the clearance. The bracket is made up in meandering form from the first basic branching portion, which bends off from the longitudinal leg in an L-shaped manner, and the consecutively adjoining second basic branching portion and third basic branching portion, the latter merging into the basic handle in an L-shaped manner. The first branching portion is adjoined in an L-shaped manner by a second branching portion. A stop leg extends inward—in the direction of the longitudinal leg—from the basic handle and bounds the through-passage on one side. The clearance, the stop leg and the through-passage, as more or less stationary elements, and the first branching portion with the second branching portion, as elements which can be deflected by way of the flexible branch, are dimensioned such that the maximum deflection of the flexible branch is defined by the second branching portion being positioned on the stop leg. The first measuring marking is provided in the form of a measurement scale—e.g. with the range 0 Ncm to 40 Ncm—at least on one of the basic branching portions, preferably on the basic branching portion adjacent to the basic handle. The second measuring marking is provided in the form of an indicator element—e.g. as a reference line or arrow—on the first or second branching portion of the flexible branch, preferably on the freely terminating, second branching portion. Conversely, it is possible for the first measuring marking to be provided in the form of an indicator element, e.g. as a reference line or arrow, on the stop leg of the basic branch, in the direction of the first branching portion of the flexible branch, in which case the second measuring marking is then provided in the form of a measurement scale, e.g. with the range 0 Ncm to 40 Ncm, on the first branching portion.

The entire torque wrench with head and neck regions, catch, shank region, indicator region and handle region, basic branch and flexible branch is produced in one piece. As an alternative, the catch may be fixed as a separate component on the torque wrench. The torque wrench is produced, at least essentially, from stainless steel, titanium, ceramic material or plastic. Laser cutting and water-jet cutting, wire-cut EDM, milling, punching, injection molding and metal diecasting are particularly suitable for the production process.

The following should be emphasized as significant advantages of the torque wrench according to the invention:

the fact that it is at least in principle in one piece is beneficial for the cleaning of the instrument, this doing away with any dismantling and often laborious reassembly;

the instrument allows reversible actuation in the ratchet mode;

it is possible to read the torque generated; and selecting a suitable material and processing method allows mass production at efficient production costs.

BRIEF DESCRIPTION OF THE ACCOMPANYING DRAWINGS

In the drawings:

FIG. 1C shows the enlarged neck region from the detail 1B with the catch removed;

FIG. 1D shows an enlarged illustration of a catch taken from FIG. 1A;

FIG. 1E shows the enlarged detail 1E from FIG. 1A;

FIG. 1F shows an enlarged illustration of the basic branch from the detail 1E;

FIG. 2A shows a front view of a first-variant conventional screwing-in instrument;

FIG. 2B shows a perspective illustration of the first-variant torque wrench according to FIG. 1A with the screwing-in instrument according to FIG. 2A in close proximity;

FIG. 5B shows the enlarged detail 5B from FIG. 5A, without the screwing-in instrument;

FIG. 5C shows the enlarged detail 5B from FIG. 5A;

FIG. 9A shows a plan view of the second-variant torque wrench according to FIG. 6A, with the second-variant screwing-in instrument according to FIG. 7 inserted, actuated in the forward direction to virtually maximum deflection of the flexible branch;

FIG. 9B shows the enlarged detail 9B from FIG. 9A;

FIG. 11A shows a plan view of a third-variant torque wrench according to the invention;

FIG. 11B shows the enlarged detail 11B from FIG. 11A;

FIG. 11C shows an enlargement of a catch taken from FIG. 11A;

FIG. 12A shows a plan view of the third-variant torque wrench according to FIG. 11A, with the second-variant screwing-in instrument according to FIG. 7 inserted, in a rest position;

FIG. 12B shows the enlarged detail 12B from FIG. 12A;

FIG. 13A shows a plan view of the third-variant torque wrench according to FIG. 11A, with the second-variant screwing-in instrument according to FIG. 7 inserted, actuated in the forward direction to virtually maximum deflection of the flexible branch;

FIG. 13B shows the enlarged detail 13B from FIG. 13A;

EXEMPLARY EMBODIMENTS

Figure 1A:
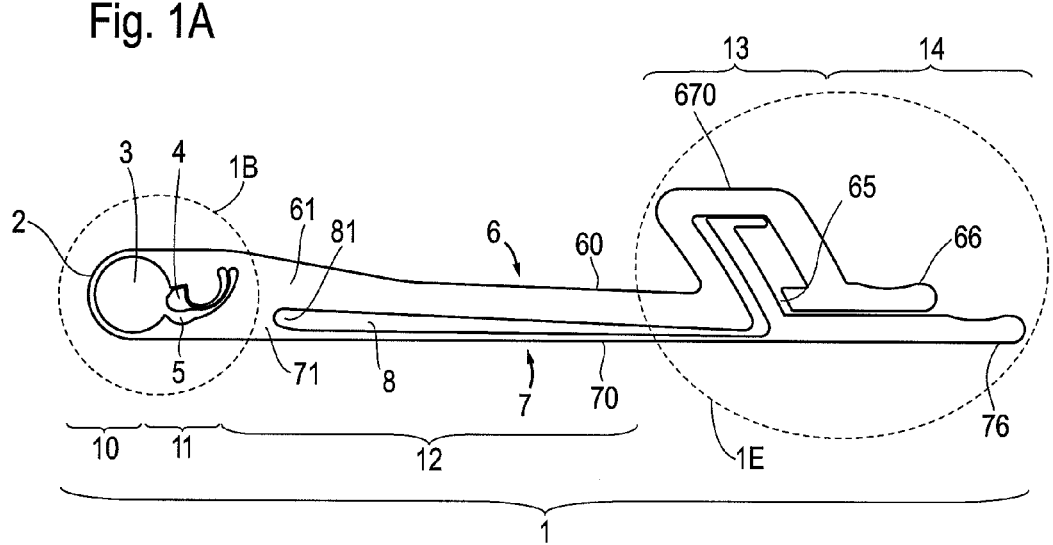
FIG. 1A shows a plan view of a first-variant torque wrench according to the invention.
Figure 1B:
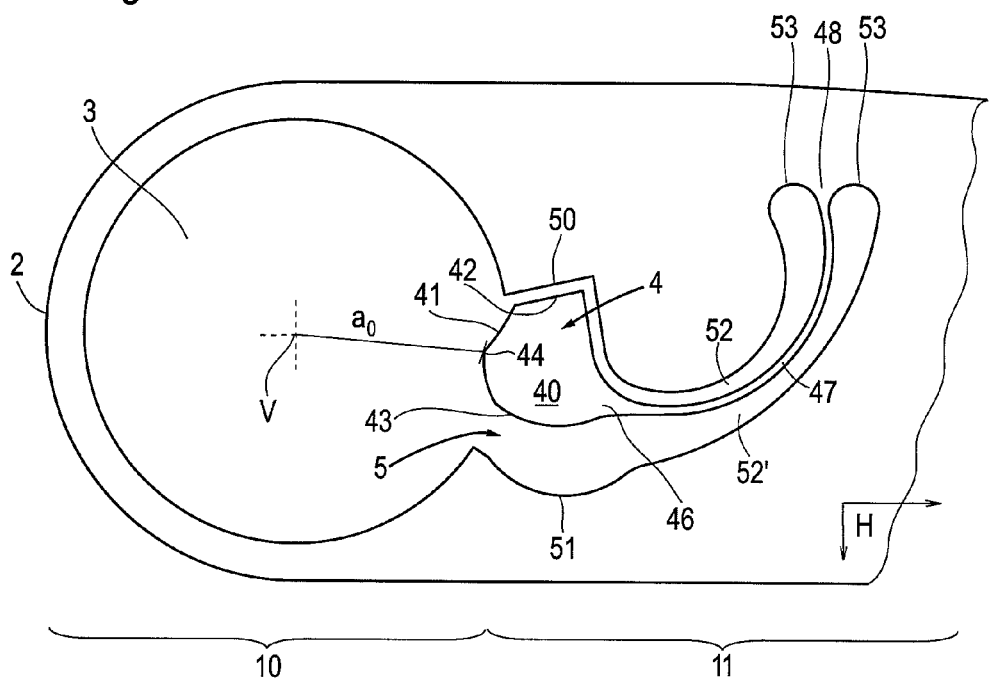
FIG. 1B shows the enlarged detail 1B from FIG. 1A.
Figure 1G:
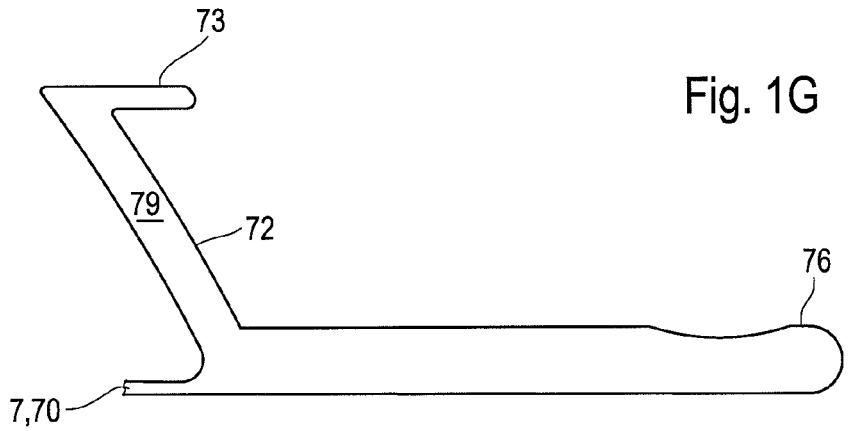
FIG. 1G shows an enlarged illustration of the flexible branch from the detail 1E.

A detailed description of an exemplary embodiment will be given hereinbelow, with reference to the accompanying drawings, in respect of the torque wrench according to the invention.

The following applies to the rest of the description: if, in order to avoid ambiguity in the drawings, a figure contains designations which are not explained in the directly associated text of the description, then you are referred to the point at which they are mentioned in previous descriptions of the figures. For reasons of clarity, components are not usually designated again in subsequent figures, provided that it is clear from the drawings that they are recurring components.

FIGS. 1A to 1G

This first series of figures describes the design of the first-variant torque wrench 1 without a screwing-in instrument 9 (see FIGS. 2A and 2B) being accommodated therein. The torque wrench 1, which advantageously comprises an elongate, flat piece of material, has, in the first instance, a head region 10, which is consecutively adjoined by a neck region 11, a shank region 12, an indicator region 13 and, finally, a handle region 14. The torque wrench 1 thus extends essentially in the direction of the plane H. The head region 10 is formed by the circular surround 2, which encloses a more or less full-circle accommodating opening 3 and opens out into the neck region 11 from two sides. The axis V extends through the center of the accommodating opening 3 and perpendicularly to the plane H. Possible materials to use are, in particular, stainless steel, titanium, ceramic material or plastic, and laser cutting and water-jet cutting, wire-cut EDM, milling, punching, injection molding or metal diecasting are preferred production methods.

The accommodating opening 3 is dimensioned in terms of diameter such that the head 90 of the screwing-in instrument 9 is placed therein without slippage. At the transition from the head region 10 to the neck region 11, a free space 5 opens out peripherally into the accommodating opening 3, which here curves into the neck region 11, it alternatively being possible for the free space 5 to extend wholly or partially in a rectilinear manner. The free space 5 contains the catch 4, which can be moved elastically to a limited extent in the plane H and is retained by a curved, leaf-like catch spring 47 which, on the one hand, merges into the catch segment 40 at a spring outlet 46 and, on the other hand, merges into the material of the neck region 11 at a spring mouth 48. To complement the alternatively rectilinear free space 5, the catch spring 47 would then likewise be rectilinear. At the peripheral mouth into the accommodating opening 3, the free space 5, which is widened here, is bounded by a first, upper stop 50—by way of example, an oblique edge—and a second, lower stop 51—by way of example, a trough 51 of preferably rounded form—located opposite the first stop. From the stops 50,51, the free space 5 continues, as a curved, channel-like upper and lower spring clearance 52,52', to the base 53, where the spring mouth 48 starts. The catch spring 47 projects, in principle, centrally through the spring clearance 52,52', so that an air gap remains as spring clearance 52,52' on both sides of the catch spring 47, this air gap allowing the spring to move.

In the non-deflected rest position, the catch segment 40 has its upper, second flank 42 located in the vicinity of the first stop 50, so that a narrow movement gap remains. The lower, third flank 43 of the catch segment 40 is at more or less the maximum distance from the second, lower stop 51. The second flank 42 is adjoined, in the direction of the accommodating opening 3, by a concave first flank 41, which extends as far as a front nose 44, which, in this case, assumes the minimum distance $a_0$ from the axis V. The front nose 44 is configured, for example, as a point or convexity which is raised in the direction of the accommodating opening 3. The third flank 43—in this case, for example, in the form of a rounded portion—follows beneath the front nose 44, and continues to the spring outlet 46. At this point in time, the second spring clearance 52', which is located on the side of the second stop 51, is wider, in the region of the second stop 51 and adjacent to this, than the first spring clearance 52, which is adjacent to the first stop 50.

From the neck region 11, beginning at the transitions 61,71, the relatively wide, rigid basic branch 6 and the narrow, resilient flexible branch 7 extend, in each case as longitudinal legs 60,70 via the shank region 12 to the indicator region 13. An air gap in the form of a cutout 8 is located between the basic branch 6 and the flexible branch 7 and allows for the elastic deflection of the flexible branch 7 independently of the basic branch 6. This cutout 8 runs from a groove base 81, which is provided adjacent to the transitions 61,71, into the indicator region 13. In the indicator region 13, the longitudinal leg 60 continues by way of first, second and third basic branching portions 62,63,64 which run in meandering fashion and, together, produce an upwardly oriented bracket 670 and enclose a clearance 67. The third basic branching portion 64 meets up in an L-shaped manner with the freely outwardly terminating basic handle 66, which is adjoined by the stop leg 65, which is oriented inward in the direction of the longitudinal leg 60. A through-passage 68 leading to the clearance 67 remains between the stop leg 65 and the connection between the longitudinal leg 60 and first basic branching portion 62.

Beneath the through-passage 68, the longitudinal leg 70 of the flexible branch 7 is followed by a first branching portion 72, which extends in the clearance 67, parallel to the first basic branching portion 62, in the direction of the second basic branching portion 63. The first branching portion 72 is adjoined in an L-shaped manner by a second branching portion 73, which runs in the clearance 67, parallel to the second basic branching portion 63, into close proximity with the third basic branching portion 64. Downstream of the start of the first branching portion 72, the longitudinal leg 70 of the flexible branch 7 merges into a handle part 76, which goes beyond the basic handle 66, as seen along the axial extent of the longitudinal leg 70.

In order for it to be possible to see the deflection to which the flexible branch 7 is subjected, and also the torque which is thus transmitted to the screwing-in instrument 9, a first measuring marking 69 is provided at least on one of the basic branching portions 62,64, while the first or second branching portion 72,73 of the flexible branch 7 has a complementary, second measuring marking 79. The first measuring marking 69 could be a measurement scale, e.g. with the range 0 Ncm to 40 Ncm, so that an indicator element in the form of a reference line or arrow, which indicates the generated torque, in the case of deflection, on the scale, is sufficient for the second measuring marking 79.

FIGS. 2A and 2B

This pair of figures shows a conventional, first-variant screwing-in instrument 9, which can have its head 90 inserted into the accommodating opening 3. The basically cylindrical head 90 has the top side 91 and the underside 92. In order to be gripped by the user, and to allow engagement by tools, the lateral surface, which is located between the top side 91 and underside 92, has conventional contouring formed by vertical grooves 93, which are preferably of rounded cross-sectional form, and vertical crosspieces 94 located therebetween. Extending from the underside 92 is a shank 96, which terminates at the instrument tip 97 and, here, has a standard profile for interacting with the screw which is to be handled.

FIG. 3A to 3D

With the screwing-in instrument 9 inserted into the accommodating opening 3 of the torque wrench 1, the instrument has its head 90 and shank 96 aligned with the axis V, which projects perpendicularly through the plane H. The cylindrical head 90 with its outer profiling, which is made up of the groove 93 and the crosspieces 94 located therebetween, is enclosed by the surround 2 of the head region 10. In the rest position, the catch segment 40 has its second flank 42 located in the vicinity of the first stop 50, and the front nose 44 assumes the minimum distance $a_0$ from the vertical axis V, the second flank 42, which is adjacent to the front nose 44, and a section of the third flank 43 ending up located in a facing groove 93, so that the crosspiece 94 adjacent to the groove 93 grips beneath part of the front of the catch segment 40. At this point in time, the second spring clearance 52' is at its maximum width in the region adjacent to the second stop 51.

Figure 4A:
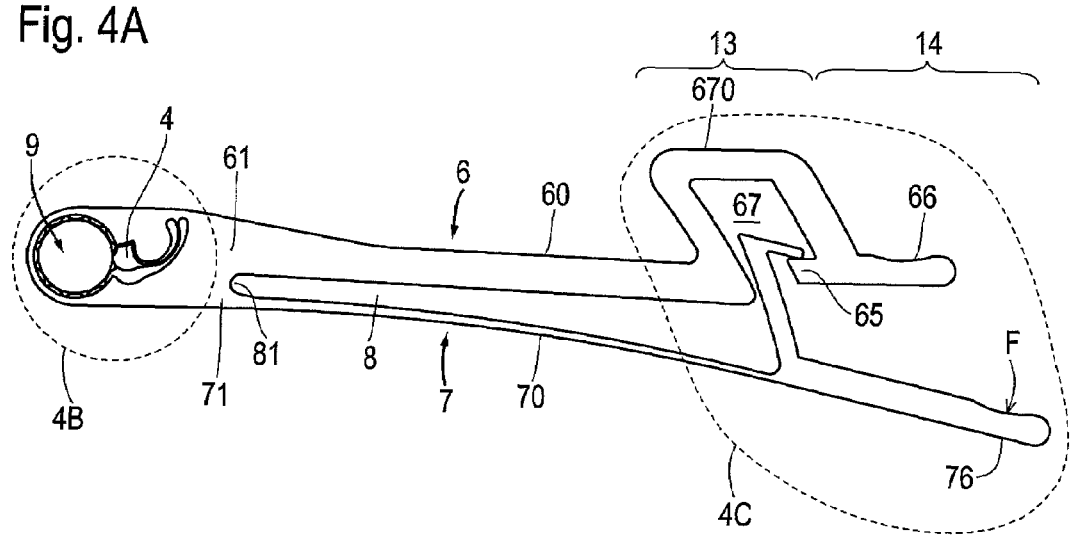
FIG. 4A shows a plan view of the first-variant torque wrench according to FIG. 1A, with the screwing-in instrument according to FIG. 2A inserted, actuated in the forward direction to the maximum deflection of the flexible branch.
Figure 4B:
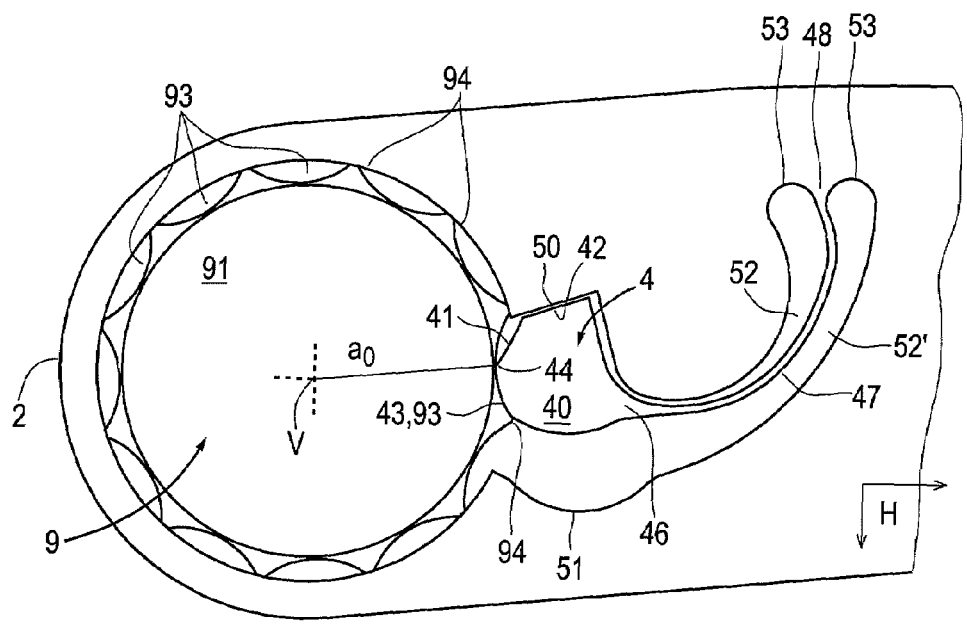
FIG. 4B shows the enlarged detail 4B from FIG. 4A.
Figure 4C:
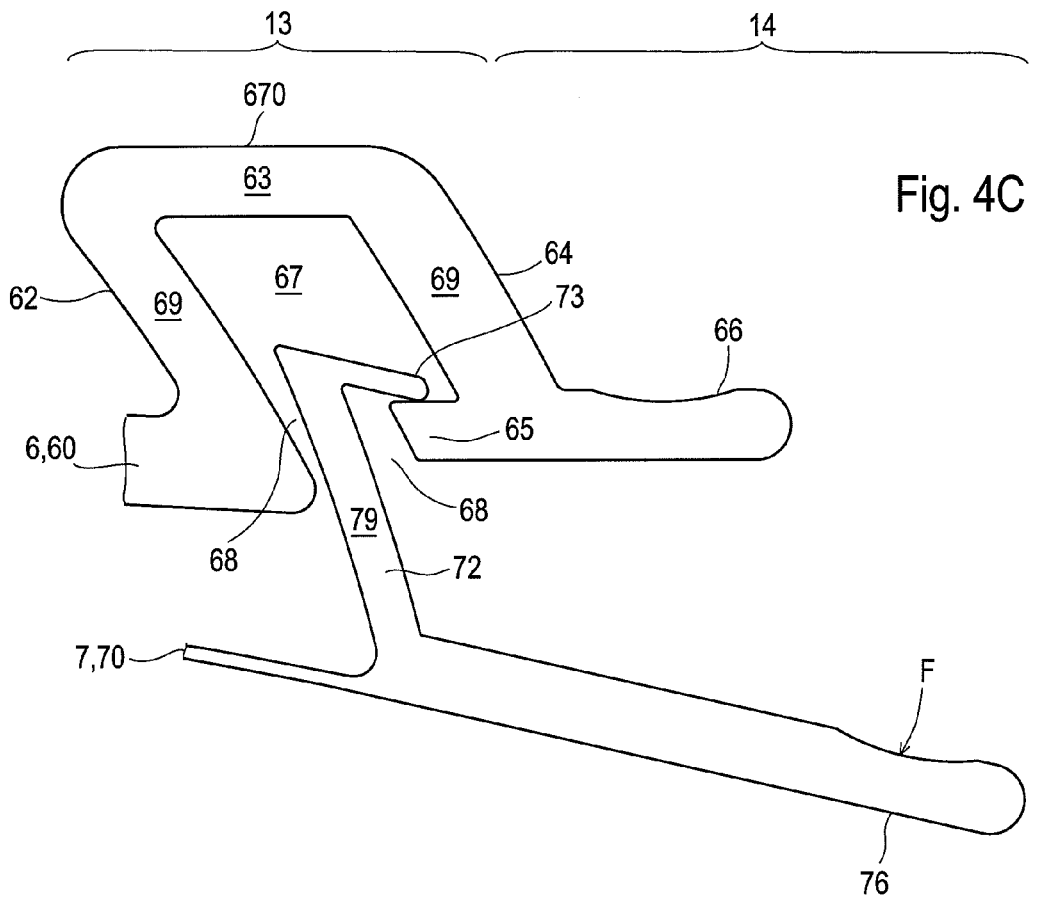
FIG. 4C shows the enlarged detail 4C from FIG. 4A.

FIGS. 4A to 4C

Figure 3A:
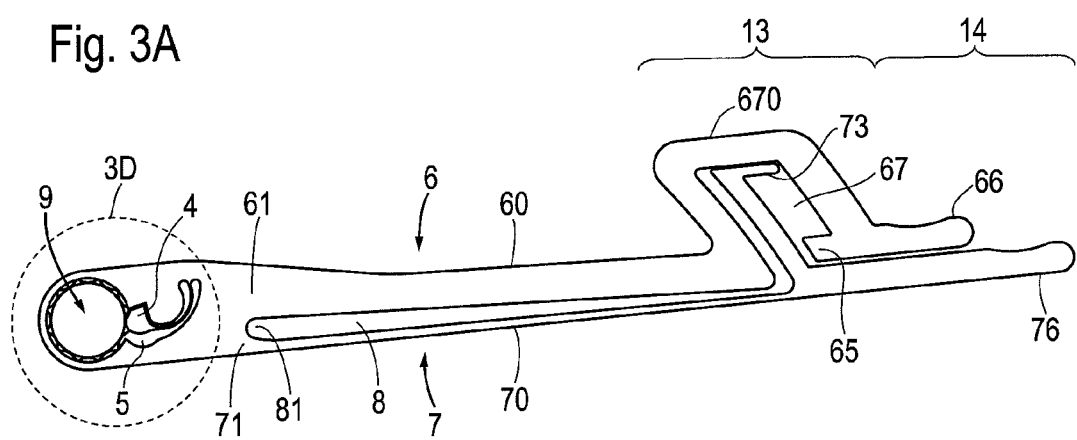
FIG. 3A shows a plan view of the first-variant torque wrench according to FIG. 1A with the screwing-in instrument according to FIG. 2A inserted, in a rest position.
Figure 3B:
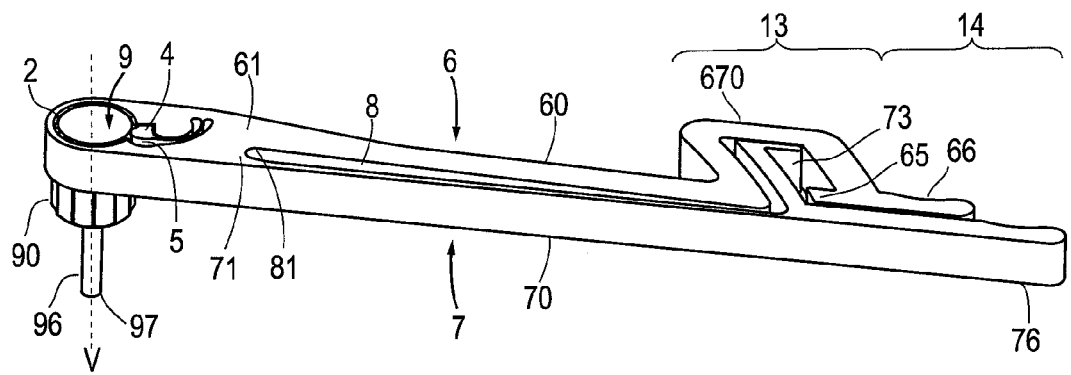
FIG. 3B shows a perspective illustration from the front of the arrangement according to FIG. 3A.
Figure 3C:
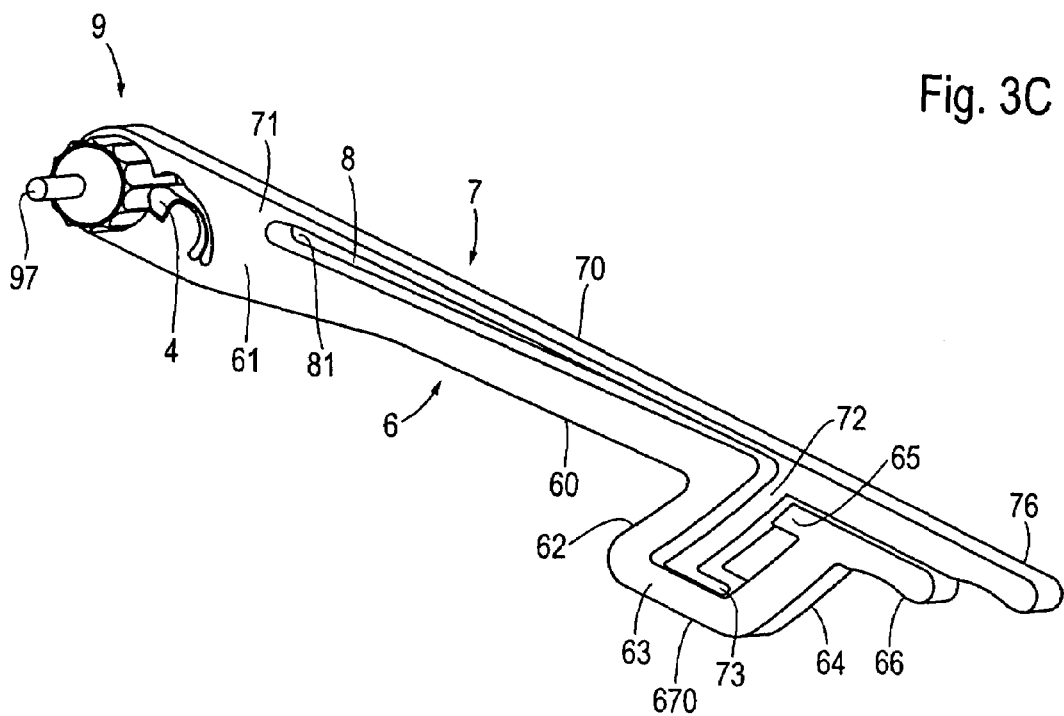
FIG. 3C shows a perspective illustration from beneath of the arrangement according to FIG. 3A.
Figure 3D:
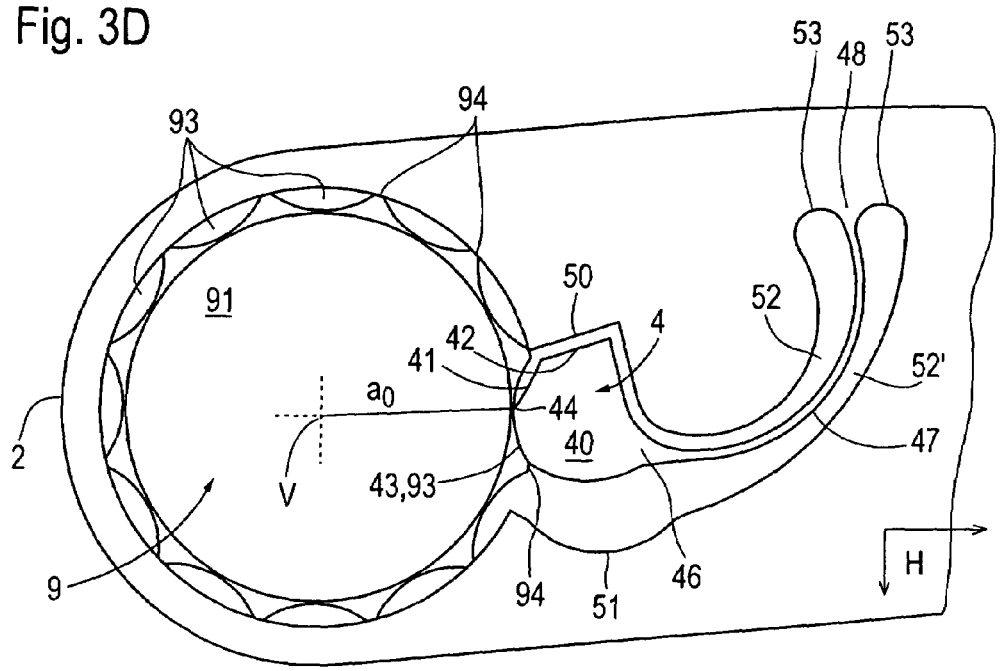
FIG. 3D shows the enlarged detail 3D from FIG. 3A.

If a forward force F is exerted on the flexible branch 7 by way of its handle part 76, this results in elastic deformation with widening of the cutout 8 in the indicator region 13, this widening decreasing into the groove base 81. In order to deflect the flexible branch 7, the user will grip the handle part 76 and move it in the clockwise direction—i.e. in the screwing-in forward direction, away from the basic handle 66—by the forward force F until the prescribed torque has been reached on the measuring markings 69,79. In order to prevent the flexible branch 7 from being over-extended, the second branching portion 73 passes against the stop leg 65 upon maximum deflection of the flexible branch 7, so that further bending is blocked. As a result of the form-fitting engagement between the front nose 44 and the adjacent third flank 43 with the facing groove 93 and the adjacent crosspiece 94, screwing in the torque wrench 1 to the right causes the screwing-in instrument 9 to be rotated along as well. As a result of the resistance occurring during the screwing-in action, the second flank 42 is pushed against the first stop 50 counter to the elasticity of the catch spring 47, so that the previously still present air gap is closed. The just small change in position of the catch segment 40 means that we can assume a basically unchanged minimum distance $a_0$ between the vertical axis V and the front nose 44. There is a difference, however, in this respect between the situations according to FIG. 3D (rest position) and FIG. 4B (loading in the screwing-in forward direction).

Figure 5A:
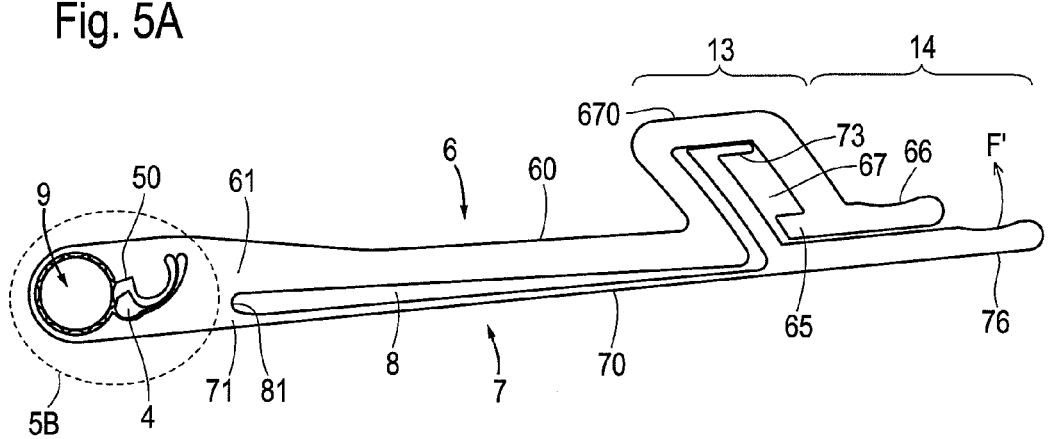
FIG. 5A shows a plan view of the first-variant torque wrench according to FIG. 1A, with the screwing-in instrument according to FIG. 2A inserted, actuated in the return direction.

FIGS. 5A to 5C

Depending on the spatial conditions, e.g. in the constricted conditions of a patient's mouth, the torque wrench 1 according to FIG. 4A has been actuated, in the screwing-in forward direction, over a possible arcuate extent, whereupon, in the case of further screwing-in action being necessary, the torque wrench 1 then has to be operated in reverse, counterclockwise mode—in its function as a ratchet instrument—in the return direction, with rotary movement about the axis V, by way of the return force F'.

In the case of the return movement, the screwing-in instrument 9 remains in position as a result of the resistance acting on the screw applied. At the same time, the catch segment 40 is guided from the first stop 50 to the second stop 51, counter to the elastic action of the catch spring 47, so that the maximum distance $a_1$ is set between the axis V and the front nose 44. The maximum distance $a_1$, once reached, allows the crosspiece 94 to move past the first flank 41 and the front nose 44. This means that, during the return movement of the torque wrench 1, the catch segment 40 can move around a plurality of crosspieces 94. Upon changeover into the forward movement again, the force which pushes the catch segment 40 in the direction of the second stop 51 is eliminated, as a result of which the catch segment 40 is guided back onto the first stop 50 by the catch spring 47 and the situation for the screwing-in action according to FIG. 4A is re-established.

Figure 6A:
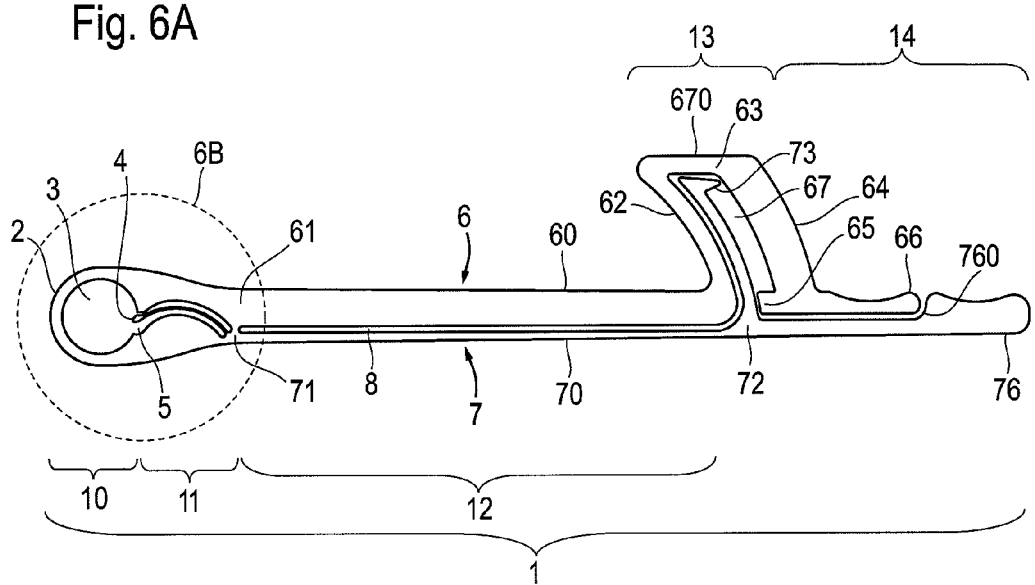
FIG. 6A shows a plan view of a second-variant torque wrench according to the invention.
Figure 6B:
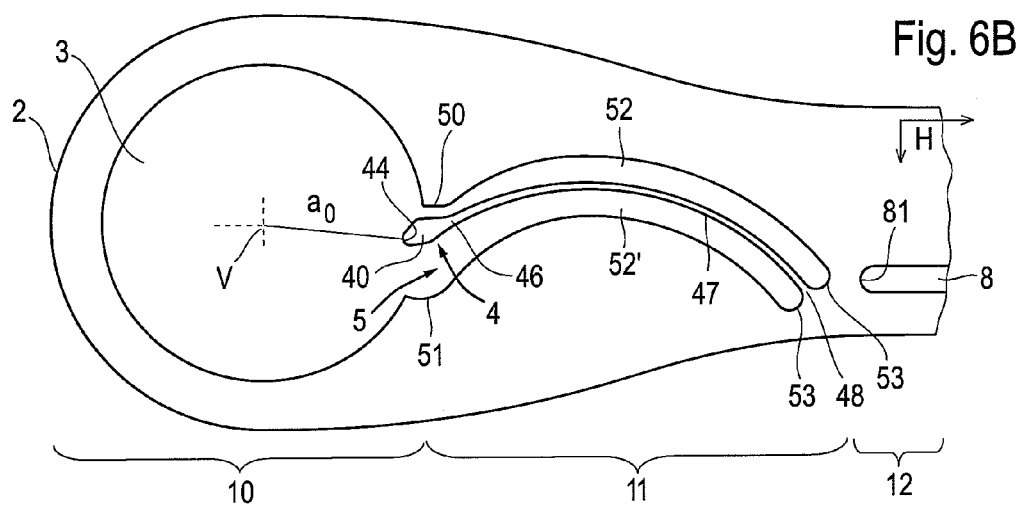
FIG. 6B shows the enlarged detail 6B from FIG. 6A.
Figure 6C:
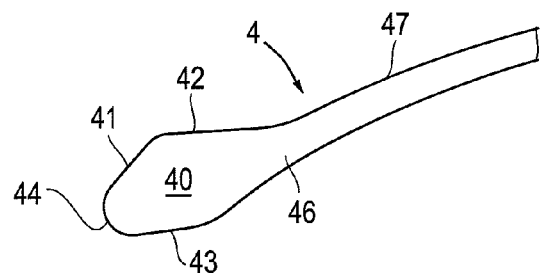
FIG. 6C shows an enlargement of a catch taken from FIG. 6A.
Figure 7:
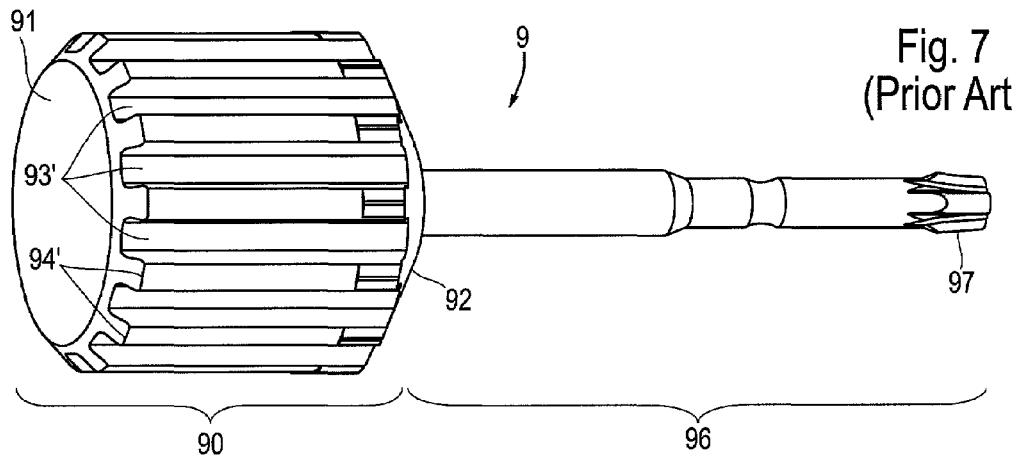
FIG. 7 shows a front view of a second-variant conventional screwing-in instrument.

FIGS. 6A to 6C

This group of figures shows a second-variant torque wrench 1 which, once again, is made up of the head region 10, the neck region 11, the shank region 12, the indicator region 13 and the handle region 14. The significant difference from the previous variant resides in the configuration of the catch 4 and of the free space 5 enclosing the same. The catch 4 and free space 5 now run convexly in relation to the lower edge of the torque wrench 1; the catch segment 40 is rather tongue-like in form and the first, upper stop 50 is formed by a shorter, basically straight edge. The head region 10 has the circular surround 2, which encloses the basically full-circle accommodating opening 3, in the center of which the axis V runs perpendicularly to the plane H. Opposite the first stop 50, the second, trough-like stop 51 is located in an unchanged state at the bottom of the mouth of the free space 5. The catch spring 47 extends from the catch segment 40, at the spring outlet 46, to the spring mouth 48 and, there, merges into the neck region 11. The first and second spring clearances 52,52' run on both sides of the catch spring 47, on the one hand terminating at the base 53, alongside the spring mouth 48 in each case, and on the other hand entering into the accommodating opening 3, alongside the catch segment 40. The catch segment 40 terminates, at the front, with the front nose 44, which projects into the accommodating opening 3 and from which a first flank 41 extends in the upward direction, this first flank merging into a second flank 42, which runs toward the spring outlet 46. In the downward direction, the front nose 44 merges into a third flank 43, which extends in the direction of the spring outlet 46. In the rest position, the axis V and the front nose 44 are spaced apart by the minimum distance $a_0$. The basic branch 6 and the flexible branch 7 extend from the transitions 61,71 at the end of the neck region 11, in the first instance, by way of their longitudinal legs 60,70, between which the cutout 8 is located, this cutout terminating, in the direction of the head region 10, in the groove base 81. On its top side, the handle part 76 has an elongate depression 760, in which the basic handle 66 is accommodated. The rest of the features are basically unchanged in relation to the first-variant torque wrench 1; this also goes for the measuring markings 69,79.

FIG. 7

The second-variant screwing-in instrument 9, once again, has the head 90 with its top side 91 and underside 92, the shank 96 extending centrally from the underside to the instrument tip 97. In contrast to the first-variant screwing-in instrument 9, the grooves 93', in this case, have a basically angular cross section and the crosspieces 94', which are located therebetween, are likewise angular, this resulting in meandering form all the way round.

Figure 8A:
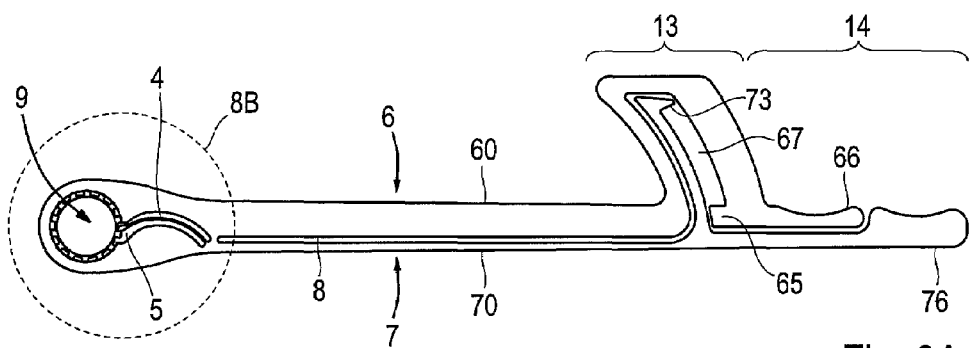
FIG. 8A shows a plan view of the second-variant torque wrench according to FIG. 6A, with the second-variant screwing-in instrument according to FIG. 7 inserted, in a rest position.
Figure 8B:
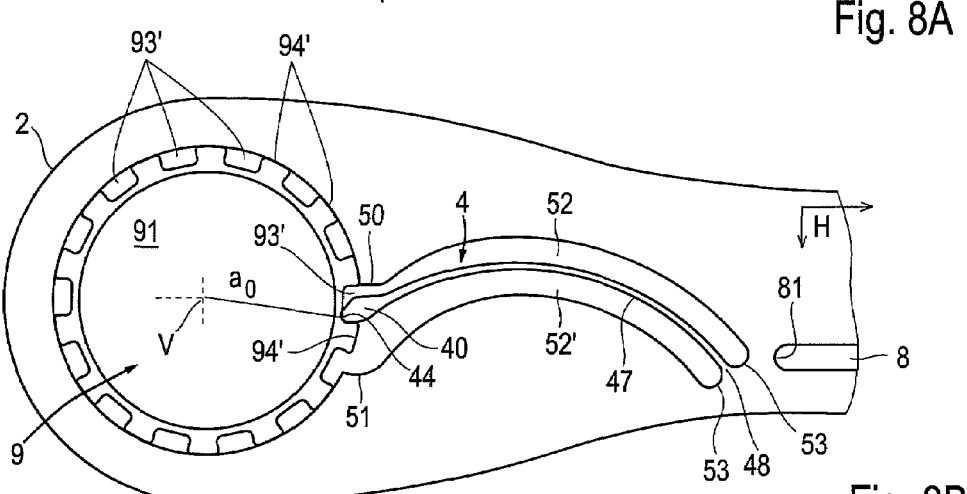
FIG. 8B shows the enlarged detail 8B from FIG. 8A.

FIGS. 8A and 8B

Once the screwing-in instrument 9 has been inserted into the accommodating opening 3 of the torque wrench 1, the head 90 and shank 96 are aligned with the axis V. The cylindrical head 90 with the profiling comprising the grooves 93' and crosspieces 94' is enclosed by the surround 2. In the rest position—the handle part 76 remains unactuated, that is to say it is neither pulled in the clockwise direction nor moved in the return direction—the catch 4 as a whole is not deflected, the catch spring 47 is thus free of stressing and the profile of the two spring clearances 52,52' remain unchanged. The catch segment 40 is spaced apart by a small distance from the first and second stops 50,51 and projects into the closest groove 93'. The minimum distance $a_0$ is present between the axis V and the front nose 44.

FIGS. 9A and 9B

This pair of figures corresponds, in principle, to FIGS. 4A to 4C and shows the second-variant torque wrench 1, with the screwing-in instrument 9 inserted, moved in the forward direction, i.e. the handle part 76 is subjected to a force F in the clockwise direction, as a result of which the flexible branch 7 has been deformed virtually to the maximum extent. The first branching portion 72 has been moved out of the clearance 67 to the greatest extent and the second branching portion 73, which serves as a stop, is located in the vicinity of the stop leg 65. At the same time, the depression 760 is fully open since the basic handle 66 is no longer located therein. The screwing-in instrument 9, which engages, for example, in a screw, is subjected to a resistance force by the tightening torque which is to be overcome, so that—depending on the magnitude of the tightening torque—the catch segment 40 is deflected in the direction of the first stop 50 by the adjacent crosspiece 94'. The front nose 44 engages to the maximum extent in a groove 93', the distance between the front nose 44 and the axis V remaining basically unchanged and, furthermore, being equal to the minimum distance $a_0$. In the case of maximum deflection, the catch segment 40 butts against the first stop 50. As a result of the catch 4 being deflected, the relationship between the spring clearances 52,52' has changed in that the first spring clearance 52 is now narrowed and the second spring clearance 52' is correspondingly widened. As long as the tightening torque is overcome by the force F acting on the handle part 76, the torque wrench 1 moves in the clockwise direction and, in the process, carries along the screwing-in instrument 9 inserted in it.

Figure 10A:
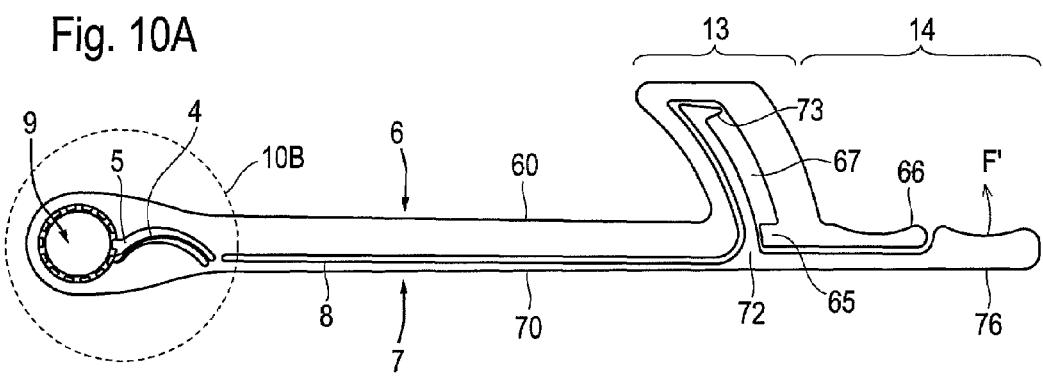
FIG. 10A shows a plan view of the second-variant torque wrench according to FIG. 6A, with the second-variant screwing-in instrument according to FIG. 7 inserted, actuated in the return direction.
Figure 10C:
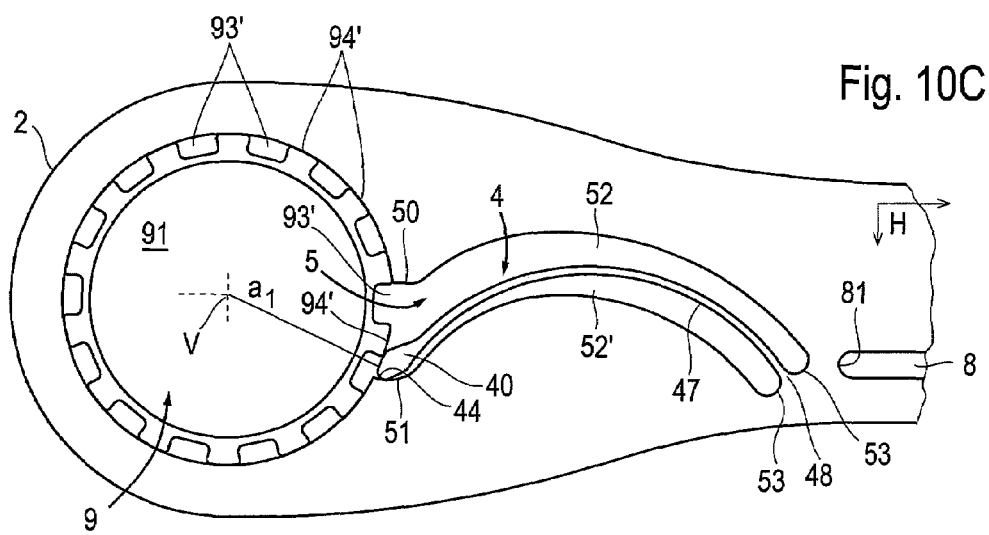
FIG. 10C shows the enlarged detail 10B from FIG. 5A.
Figure 10B:
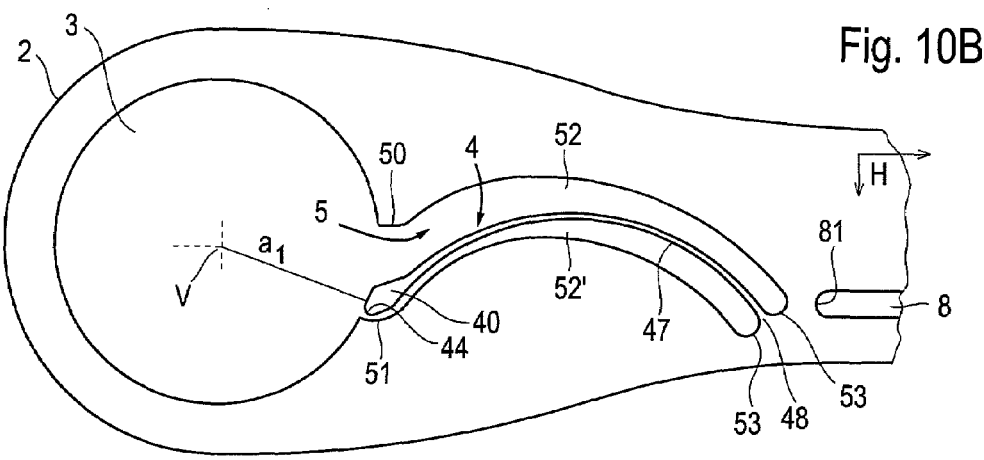
FIG. 10B shows the enlarged detail 10B from FIG. 10A, without the screwing-in instrument.

FIGS. 10A to 10C

This group of figures corresponds, in principle, to FIGS. 5A to 5C and shows the second-variant torque wrench 1, with the screwing-in instrument 9 inserted, moved in the return direction, i.e. a counterclockwise force F' acts on the handle part 76. The basic branch 6 and the flexible branch 7 are located in close proximity to one another; the latter and the cutout 8 are not deformed. The first branching portion 72 and the second branching portion 73 have been moved all is the way into the clearance 67. The release torque, which has not been overcome, causes the screwing-in instrument 9 to be at a standstill, as a result of which the crosspiece 94' following the catch segment 40 causes the catch 4 to be deflected. Consequently, the catch segment 40 is pushed in the direction of the second stop 51 and the maximum distance $a_1$ is set between the catch segment 40 and the axis V, so that—apart from the contact with the circular surface of the crosspieces 94'—the catch segment 40 is disengaged from the head 90 of the screwing-in instrument 9. Bending of the catch spring 47 then results in widening of the first spring clearance 52, while the second spring clearance 52' has narrowed.

FIGS. 11A to 12B

These figures show a third-variant torque wrench 1. The only modifications are the catch 4 as a whole, with the catch segment 40, and the profile of the catch spring 47 and also the free space 5 with the adjacent first, upper stop 50 and the trough-like second, lower stop 51. The catch segment 40, in this case, has more of an angular tongue shape, and terminates at the front by way of the front nose 44 which projects into the accommodating opening 3 and from which the first flank 41 runs upward, this first flank being adjoined by a second flank 42, which meets up with the spring outlet 46. The front nose 44 is followed in the downward direction by a third flank 43, which merges into the spring outlet 46. The free space 5 in this case scrolls within the neck region 11, in the direction of the base 53, from the mouth into the accommodating opening 3. The catch spring 47 runs through the free space 5 in a likewise scroll-like manner, divides off the free space 5, once again, into a first and a second spring clearance 52,52', and terminates at the spring mouth 48. The first stop 50 is relatively steep, and the catch segment 40, in the current rest position, is spaced apart by the minimum distance $a_0$ from the axis V. The trough contour of the lower stop 51 is relatively pronounced. All the rest of the elements of the torque wrench 1 are unchanged in relation to the previous variants; this also goes for the measuring markings 69,79.

It is also the case that the second-variant screwing-in instrument 9 is inserted into the third-variant torque wrench 1. In the rest position—neither a forward force F nor a return force F' acts on the handle part 76, and the basic handle 66 is located in the depression 76O—the front nose 44 projects all the way into a groove 93' and the catch 4 as a whole, with the catch segment 40 and the catch spring 47 projecting therefrom, is not deflected within the free space 5. The catch segment 40 is spaced apart from the two stops 50,51.

FIGS. 13A and 13B

Upon actuation of the third-variant torque wrench 1, with the second-variant screwing-in instrument 9 inserted, in the forward direction—a forward force F acts on the deflected handle part 76—the situation is analogous to that in FIGS. 4A to 4C and also 9A and 9B. It is only the position of the catch 4 and the interaction of the latter with the screwing-in instrument 9 which are different, on account of the modifications to the catch 4, free space 5 and the adjacent contours. The resistance to which the screwing-in instrument 9 is subjected causes the catch segment 40, which has its front nose 44 located in a groove 93', to be pushed against the first stop 50, the catch spring 47 also being deflected and the relationship between the two spring clearances 52,52' thus shifting. The minimum distance $a_0$ between the front nose 44 and the axis V is maintained in principle.

Figure 14A:
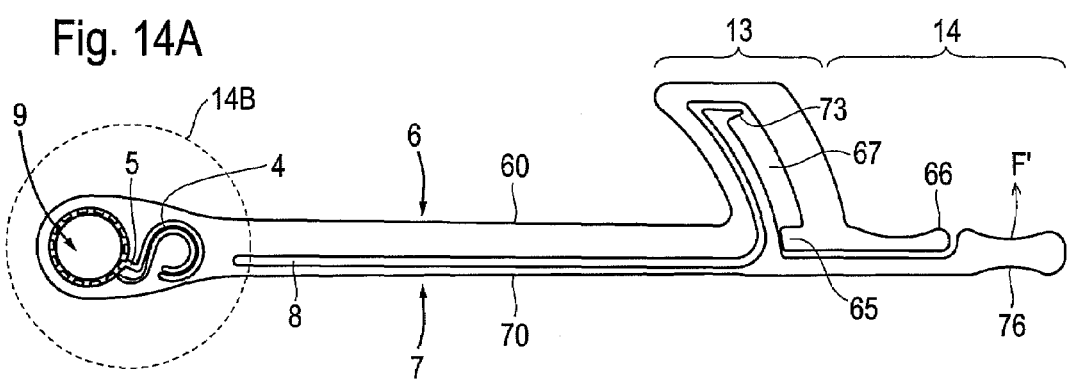
FIG. 14A shows a plan view of the third-variant torque wrench according to FIG. 11A, with the second-variant screwing-in instrument according to FIG. 7 inserted, actuated in the return direction.
Figure 14C:
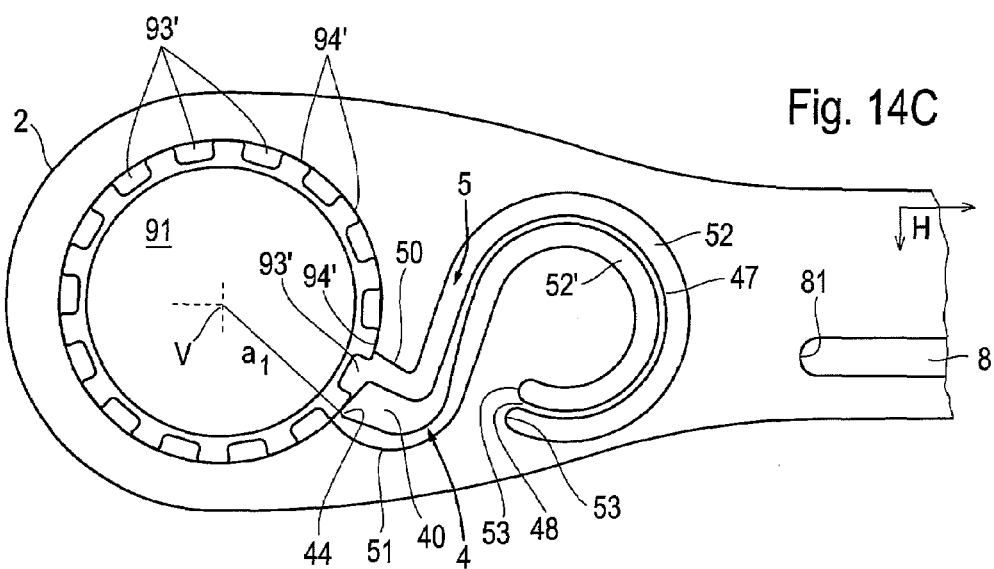
FIG. 14C shows the enlarged detail 14B from FIG. 14A.
Figure 14B:
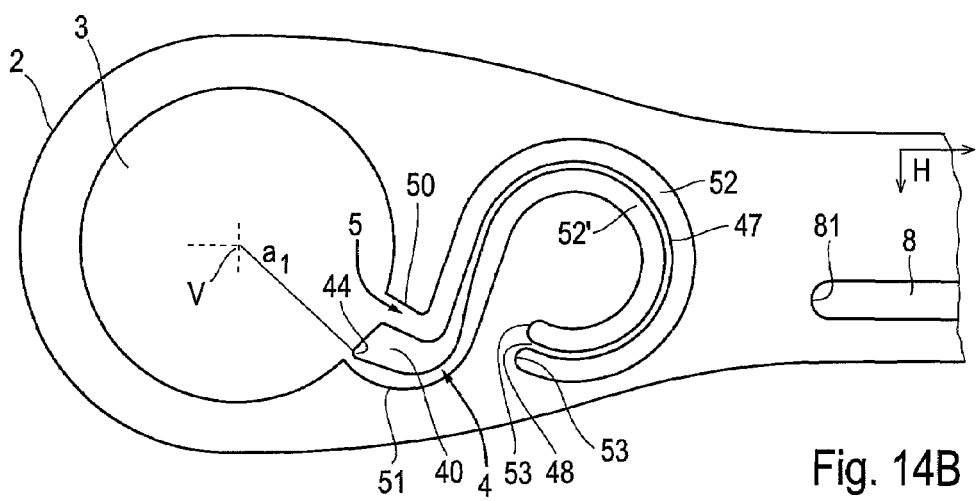
FIG. 14B shows the enlarged detail 14B from FIG. 14A, without the screwing-in instrument.

FIGS. 14A to 14C

This group of figures illustrates the third-variant torque wrench 1, with the second-variant screwing-in instrument 9 inserted, upon actuation in the return direction, i.e. the return force F' acts on the handle part 76. As a result of the arrested position of the screwing-in instrument 9, the front nose 44 of the catch segment 40 is moved out of the previously occupied groove 93' onto the circular surface of the crosspieces 94' and the catch 4 as a whole is deflected, the catch segment 40 moving in the direction of the second stop 51. The front nose 44 moves to the maximum distance $a_1$ from the axis V, and the second spring clearance 52' narrows in particular in the region of the second stop 51, while the first spring clearance 52 widens in particular in the region of the first stop 50.

The invention claimed is:

1. A torque wrench (1) as a ratchet instrument for the medical field, having:
    a front and a rear, a head region (10) located at the front, an adjoining neck region (11), a shank region (12) adjacent to the neck region (11), and a handle region (14) arranged at the rear, the head, neck, and shank regions extending in a plane (H); an accommodating opening (3) provided in the head region (10);
    a surround (2) enclosing the opening (3);
    the opening has a center point through which an axis (V) extends vertically; and the opening is sized to allow a conventional screwing-in instrument (9) to be inserted along the extent of the axis (V), which is perpendicular to the plane (H);
    a catch segment (40) is arranged on the periphery of the accommodating opening (3), the catch segment (40) is sized to move to a limited extent and the front portion (41-44) of the catch segment (40) is oriented toward the accommodating opening (3), the front portion (41-44) is sized to: upon actuation of the torque wrench (1) in the forward direction, come into carry-along engagement with an outer contour (93,94;93',94') provided on a head (90) of the screwing-in instrument (9); and upon actuation of the torque wrench (1) in the return direction, release the carry-along engagement with the outer contour (93,94;93',94') provided on the head (90) of the screwing-in instrument (9); and
    a flexurally rigid basic branch (6) is sized to run along the torque wrench (1) from the neck region (11), wherein
    a deflectable branch (7) is provided via which, upon actuation of the torque wrench (1) in the forward direction, the torque which is to be generated is introduced by means of a forward force (F) exerted by the user;
    a catch spring (47) is sized to extend into the neck region (11) from the catch segment (40), the catch segment (40) and the catch spring (47) forming a single-piece catch (4);
    the catch segment (40) and catch spring (47) are arranged in the channel-like free space (5), which allows the catch segment (40) and catch sprint (47) to be deflected in the plane (H) counter to the force of the catch spring (47); and the catch (4) is formed integrally from the neck region (11), the catch segment (40) has, on its front portion (41-44), a front nose (44), to one side of which is located a second flank (42) and to the other side of which is located a third flank (43); the free space (5) opens out into the accommodating opening (3) by a first and a second stop (50,51);
    the first stop (50) is arranged opposite the second flank (42) and, upon actuation of the torque wrench (1) in the forward direction, the second flank (42) of the at least basically non-deflected catch (4) butts against the first stop (50), the front nose (44) being spaced apart by the minimum distance ($a_0$) from the axis (V); and
    the second stop (51) is arranged opposite the third flank (43) and, upon actuation of the torque wrench (1) in the return direction, the third flank (43) of the deflected catch (4) has moved toward the second stop (51) or butts against the same, in which the front nose (44) is spaced apart by the maximum distance ($a_1$) from the axis (V), the second flank (42) is remote from the first stop (50) and the catch spring (47) has been elastically deformed counter to its restoring force, wherein the catch spring (47) merges into the catch segment (40) at a spring outlet (46) and, merges into the neck region (11) at a spring mouth (48); and is in the form of a rectilinear or at least partially curved leaf spring;

the front nose (44) of the catch segment (40) is followed, in one direction, by a first flank (41), the first flank (41) being adjoined by the second flank (42);

is followed, in the other direction, by the third flank (43), which extends in a rounded manner in the direction of the spring outlet (46); the front nose (44) being designed as a point or convexity which is raised in the direction of the accommodating opening (3); the first stop (50) is formed as a straight edge and the second stop (51) is of trough-like form; and the catch spring (47), which projects through the free space (5), divides off a first and a second spring clearance (52,52'), the proportions of which change as the catch spring (47) moves, and which terminate in a base (53) which is followed by the spring mouth (48).

2. The torque wrench (1) as claimed in claim 1, wherein the basic branch (6) extends, in the first instance as a longitudinal leg (60), from a transition (61) located in the neck region (11), via the shank region (12), into an indicator region (13) and terminates freely in the handle region (14) by a basic handle (66);

the flexible branch (7) runs, in the first instance as an elongate longitudinal leg (70) and parallel to the longitudinal leg (60), into the indicator region (13) from a transition (71) located in the neck region (11), and terminates freely in the handle region (14) by a handle part (76), which projects beyond the basic handle (66);

the flexible branch (7) has on its top side, directed toward the basic branch (6), a depression (760), in which the stop leg (65) and the basic handle (66) are partially embedded; and a cutout (8) is located between the longitudinal leg (60) of the basic branch (6) and the longitudinal leg (70) of the flexible branch (7) and extends into the indicator region (13) from a groove base (81) adjacent to the transitions (61,71).

3. The torque wrench (1) as claimed in claim 2, wherein the indicator region (13) is formed by at least one branching portion (62,63,64) of the basic branch (6), the portion being located between the longitudinal leg (60) and the basic handle (66); at least one branching portion (72,73) of the flexible branch (7), this branching portion being located between the longitudinal leg (70) of the flexible branch and the handle part (76); and as the torque wrench (1) is actuated in the forward direction and the flexible branch (7) is deflected, the relative positioning between the at least one branching portion (62, 63,64) of the basic branch (6) and the at least one branching portion (72,73) of the flexible branch (7), starting from the rest position or zero position, undergoes an incremental change which is a measure of the torque generated.

4. The torque wrench (1) as claimed in claim 3, wherein a first and a second measuring marking (69,79) are respectively provided on the at least one branching portion (62,63,64) of the basic branch (6) and the at least one branching portion (72,73) of the flexible branch (7), it being possible to read from these measuring markings the deflection of the flexible branch (7), due to the forward force (F) acting thereon, as the torque generated.

5. The torque wrench (1) as claimed in claim 4, wherein the indicator region (13) comprises a bracket (670) which extends from the longitudinal leg (60) to the basic handle (66), is formed by the at least one branching portion (62,63,64) and encloses a clearance (67) for which a through-passage (68) is provided; and the at least one branching portion (72,73) of the flexible branch (7), this branching portion projecting through the through-passage (68) into the clearance (67).

6. The torque wrench (1) as claimed in claim 5, wherein the bracket (670) is made up in meandering form from the first basic branching portion (62), which bends off from the longitudinal leg (60) in an L-shaped manner, and the consecutively adjoining second basic branching portion (63) and third basic branching portion (64), the latter merging into the basic handle (66) in an L-shaped manner; the first branching portion (72) is adjoined in an L-shaped manner by a second branching portion (73);

a stop leg (65) extends inward, in the direction of the longitudinal leg (60), from the basic handle (66) and bounds the through-passage (68) on one side; wherein the clearance (67), the stop leg (65) and the through-passage (68), as more or less stationary elements, and the first branching portion (72) with the second branching portion (73), as elements which can be deflected by the flexible branch (7), are dimensioned such that the maximum deflection of the flexible branch (7) is defined by the second branching portion (73) being positioned on the stop leg (65).

7. The torque wrench (1) as claimed in claim 6, wherein the first measuring marking (69) is provided in the form of a measurement scale, at least on one of the basic branching portions (62,64); and the second measuring marking (79) is provided in the form of an indicator element on the first or second branching portion (72,73) of the flexible branch (7); or the first measuring marking (69) is provided in the form of an indicator element on the stop leg (65) of the basic branch (6), in the direction of the first branching portion (72) of the flexible branch (7); and the second measuring marking (79) is provided in the form of a measurement scale on the first branching portion (72).

8. The torque wrench (1) as claimed in claim 7, wherein the entire torque wrench (1) with head region (10), neck region (11), catch (4), shank region (12), indicator region (13), handle region (14), basic branch (6) and flexible branch (7) is produced in one piece.

9. The torque wrench (1) as claimed in claim 8, wherein the torque wrench (1) is produced from a material from the group comprising stainless steel, titanium, ceramic material and plastic; and is produced by a method from the group comprising laser cutting and water-jet cutting, wire-cut EDM, milling, punching, injection molding and metal diecasting.

10. The torque wrench (1) as claimed in claim 9, wherein the branch (7) is linearly elastic flexible.

* * * * *